US008071357B2

(12) United States Patent
Sawai et al.

(10) Patent No.: US 8,071,357 B2
(45) Date of Patent: Dec. 6, 2011

(54) YEAST AND METHOD OF PRODUCING L-LACTIC ACID

(75) Inventors: Hideki Sawai, Kamakura (JP); Kenji Sawai, Kamakura (JP); Tomonori Sonoki, Kamakura (JP); Satoko Hatahira, Fujisawa (JP)

(73) Assignee: Toray Industries, Inc. (JP)

( * ) Notice: Subject to any disclaimer, the term of this patent is extended or adjusted under 35 U.S.C. 154(b) by 613 days.

(21) Appl. No.: 12/083,315

(22) PCT Filed: Sep. 4, 2006

(86) PCT No.: PCT/JP2006/317446
§ 371 (c)(1),
(2), (4) Date: May 5, 2008

(87) PCT Pub. No.: WO2007/043253
PCT Pub. Date: Apr. 19, 2007

(65) Prior Publication Data
US 2009/0239274 A1    Sep. 24, 2009

(30) Foreign Application Priority Data
Oct. 14, 2005  (JP) ................................. 2005-300415

(51) Int. Cl.
C12N 1/00 (2006.01)
C12N 1/11 (2006.01)
C12N 1/16 (2006.01)
(52) U.S. Cl. .................. 435/254.2; 435/243; 435/252.3; 435/254.1; 435/254.21; 435/255.1
(58) Field of Classification Search ............... 435/254.2, 435/243, 252.3, 254.1, 254.21, 255.1
See application file for complete search history.

(56) References Cited

U.S. PATENT DOCUMENTS

| 5,712,152 | A | 1/1998 | Dequin et al. |
| 6,429,006 | B1 | 8/2002 | Porro et al. |
| 6,485,947 | B1 | 11/2002 | Rajgarhia et al. |
| 6,723,837 | B1 * | 4/2004 | Karunanandaa et al. .... 536/23.1 |
| 2003/0166179 | A1 | 9/2003 | Rajgarhia et al. |
| 2003/0228671 | A1 | 12/2003 | Hause et al. |
| 2003/0233675 | A1 * | 12/2003 | Cao et al. ...................... 800/279 |
| 2005/0120394 | A1 | 6/2005 | Saitoh et al. |

FOREIGN PATENT DOCUMENTS

| JP | 8-48697 A | 2/1996 |
| JP | 2001-204464 | 7/2001 |
| JP | 2001-204468 | 7/2001 |
| JP | 2001204464 | 7/2001 |
| JP | 2001204468 | 7/2001 |
| JP | 2001-516584 | 10/2001 |
| JP | 2003-93060 A | 4/2003 |
| JP | 2003-259878 A | 9/2003 |
| JP | 2006-6271 A | 1/2006 |
| JP | 2006020602 | 1/2006 |
| JP | 2006-280368 A | 10/2006 |
| JP | 2008-029329 | 2/2008 |
| JP | 2008-048726 | 3/2008 |
| JP | 2008-283917 | 11/2008 |
| WO | WO 99/14335 A1 | 3/1999 |
| WO | WO 03/102152 A2 | 12/2003 |
| WO | WO 2004/065552 A2 | 8/2004 |
| WO | WO 2004/071405 A2 | 8/2004 |
| WO | WO 2004/088274 A2 | 10/2004 |

OTHER PUBLICATIONS

Rudinger, J., "Characteristics of the amino acids as components of a peptide hormone sequence", in Peptide Hormones, University Park Press: Baltimore, MD, pp. 1-7, 1976.*
Watson et al., Recombinant DNA, Second Edition, 2001. .pp. 153-154.*
Voet et al Biochemistry, John Wiley and Sons, 1990, pp. 126-128.*
Ngo, in the Protein Folding Problem and Tertiary Structure Prediction, Merz et al. (eds.*
Kimchi-Sarfaty et al., 2007, Science, pp. 525-528.*
Karunanandaa,B., et al., SCORE Search Results Details for U.S. Appl. No. 12/083,315 and Search Result 20101123_111541_us-12-083-315-53.rge Results NO1.*
Cao et alSCORE Search Results Details for U.S. Appl. No. 12/083,315 and Search Result 20101123111540_us-12-083-315-53.rng.*
Tsuji S,et al., Proc Natl Acad Sci U S A. Sep. 27, 1994;91(20):9392-6.Evolutionary relationships of lactate dehydrogenases (LDHs) from mammals, birds, an amphibian, fish, barley, and bacteria: LDH cDNA sequences from Xenopus, pig, and rat.*
"Xenopus Laevis Lactate Dehydrogenase A2 (ldha2) MRNA, complete eds.", 1999, XP002560682.
"Xenopus Laevis Lactate Dehydrogenase A, mRNA (cDNA clone MGC: 53139 Image: 5542650), complete cds", 2003, XP002560684.
Klein, Steven et al., "Genetic and Genomic Tools for *Xenopus* Research: The NIH Xenopus Initiative," 2002, vol. 225; No. 4, pp. 384-391, *Development Dynamics*, XP002560685.
Tsujibo, Hiroshi et al., "Nucleotide Sequences of the cDNA and an Intronless Pseudogene or Human Lactate Dehydrogenase—A Isozyme," *Eur. J. Biochem.*, 1985, vol. 147, pp. 9-15.
Porro, Danilo et al., "Development of Metabolically Engineered *Saccharomyces cerevisiae* Cells for the Production of Lactic Acid," *Biotechnol. Prog.*, 1995, vol. 11, pp. 294-298.
Porro, Danilo et al., "Replacement of a Metabolic Pathway for Large-Scale Production of Lactic Acid from Engineered Yeasts," *Applied and Environmental Microbiology*, Sep. 1999, vol. 65, No. 9, pp. 4211-4215.
Mannen, Hideyuki et al., "Molecular Evidence for a Clade of Turtles," *Molecular Phylogenetics and Evolution*, Oct. 1999, vol. 13, No. 1, pp. 144-148.
Saitoh, Satoshi et al., "Genetically Engineered Wine Yeast Produces a High Concentration of L-Lactic Acid of Extremely High Optical Purity," *Applied and Enviromental Microbiology*, May 2005, vol. 71, No. 5, pp. 2789-2792.

* cited by examiner

Primary Examiner — Maria Leavitt
(74) Attorney, Agent, or Firm — DLA Piper LLP (US)

(57) ABSTRACT

Yeast includes an introduced gene coding a *Homo sapiens*- or frog-derived L-lactate dehydrogenase. It is possible to produce lactic acid, which has a variety of applications, efficiently and more cost-effectively by using the yeast and the method of producing lactic acid by using the yeast.

9 Claims, 3 Drawing Sheets

SEQUENCE LISTING

```
<160> NUMBER OF SEQ ID NOS: 64

<210> SEQ ID NO 1
<211> LENGTH: 999
<212> TYPE: DNA
<213> ORGANISM: Homo sapiens

<400> SEQUENCE: 1
atggcaactc taaaggatca gctgatttat aatcttctaa aggaagaaca gacccccag      60 aataagatta cagttgttgg ggttggtgct gttggcatgg cctgtgccat cagtatctta    120
atgaaggact tggcagatga acttgctctt gttgatgtca tcgaagacaa attgaaggga    180
gagatgatgg atctccaaca tggcagcctt ttccttagaa caccaaagat tgtctctggc    240
aaagactata atgtaactgc aaactccaag ctggtcatta tcacggctgg ggcacgtcag    300
caagagggag aaagccgtct taatttggtc cagcgtaacg tgaacatatt taaattcatc    360
attcctaatg ttgtaaaata cagcccgaac tgcaagttgc ttattgtttc aaatccagtg    420
gatatcttga cctacgtggc ttggaagata agtggttttc ccaaaaaccg tgttattgga    480
agtggttgca atctggattc agcccgattc cgttacctga tgggggaaag gctgggagtt    540
cacccattaa gctgtcatgg gtgggtcctt ggggaacatg gagattccag tgtgcctgta    600
tggagtggaa tgaatgttgc tggtgtctct ctgaagactc tgcacccaga tttagggact    660
gataaagata aggaacagtg gaaagaggtt cacaagcagg tggttgagag tgcttatgag    720
gtgatcaaac tcaaaggcta cacatcctgg gctattggac tctctgtagc agatttggca    780
gagagtataa tgaagaatct taggcgggtg cacccagttt ccaccatgat taagggtctt    840
tacggaataa aggatgatgt cttccttagt gttccttgca ttttgggaca gaatggaatc    900
tcagaccttg tgaaggtgac tctgacttct gaggaagagg cccgtttgaa gaagagtgca    960
gatacacttt ggggggatcca aaaggagctg caattttaa                           999

<210> SEQ ID NO 2
<211> LENGTH: 999
<212> TYPE: DNA
<213> ORGANISM: Xenopus laevis

<400> SEQUENCE: 2
atggcaactg tgaaggataa actcatccac aatgtggtca aggaggagtc gctcccccag      60
aacaaggtca ccattgtggg tgtgggggcc gtgggcatgg cctgtgccat cagtgtcctg    120
cagaaggatt tggcagatga gcttgcactt gttgatgtga tagaagacaa actgaagggg    180
gaaatgatgg atctccagca tggcagtctg ttccttcgta cccccaagat tgtctcaggg    240
aaagattaca gcgtcactgc aaactccaag ctggtagttg tgacggccgg ggcccgtcag    300
caggagggag agagtcgcct gaatctggtt cagcgcaatg tcaacatctt caaattcatc    360
attcccaaca ttgtcaagta cagccccaac tgcacccctg tcatcgtctc caacccagtg    420
```

```
gacattctga catatgtggc ctggaagatc agtggattcc ccaaaaaccg tgtcattggc      480
agcggctgca atttggactc tgcccgtttc cgttacctca tggggcagaa gtttgggatc      540
cacacccaga gctgccacgg ttgggtcatt ggggaacacg gagactcgag tgtgccagtg      600
tggagtgggg tgaatgtggc tggcgtgtcc ctgaaaaccc tgcacccga tattgggagt       660 gacgcagaca aggagaactg gaaggaggtg cacaagcagg ttgtggacag cgcctatgaa      720
gtgatcaagc tgaagggcta cacctcctgg gctattggcc tgtccgtagc tgacctgtct     780
gagagtatcc tgaagaacct ccgccgagtc catcccattt ccacaatggt caagggcatg     840
tacggcgtga ataatgatgt tttcctcagt gtccctgtg tgttgggcaa cttgggcatc      900
acagacgtgg ttaacatgac gctgaaggca gatgaagagg atcgcttacg caagagcgca     960 gacacctgt gggccatcca gaaggagctg cagttctag                              999
```

```
<210> SEQ ID NO 3
<211> LENGTH: 999
<212> TYPE: DNA
<213> ORGANISM: Bos taurus

<400> SEQUENCE: 3
atggcaactc tcaaggatca gctgattcag aatcttctta aggaagaaca tgtcccccag       60
aataagatta caattgttgg ggttggtgct gttggcatgg cctgtgccat cagtatctta     120
atgaaggact ggcagatgaa agttgctctt gttgatgtca tggaagataa actgaaggga     180
gagatgatgg atctccaaca tggcagcctt ttccttagaa caccaaaaat tgtctctggc     240
aaagactata atgtgacagc aaactccagg ctggttatta tcacagctgg ggcacgtcag     300
caagagggag agagccgtct gaatttggtc cagcgtaacg tgaacatctt taaattcatc     360
attcctaata ttgtaaaata cagcccaaat tgcaagttgc ttgttgtttc caatccagtc     420
gatattttga cctatgtggc ttggaagata agtggcttc ccaaaaaccg tgttattgga      480
agtggttgca atctggattc agctcgcttc cgttatctca tgggggagag ctgggagtt      540 cacccattaa gctgccatgg gtggatcctg ggggagcatg gtgactctag tgtgcctgta     600
tggagtggag tgaatgttgc tggtgtctcc ctgaagaatt tacaccctga attaggcact     660
gatgcagata aggaacagtg gaaagcggtt cacaaacaag tggttgacag tgcttatgag     720
gtgatcaaac tgaaggcta cacatcctgg gccattggac tgtcagtggc cgatttggca     780
gaaagtataa tgaagaatct taggcgggtg catccgattt ccaccatgat taagggtctc     840 tatgaataa aagaggatgt cttccttagt gttccttgca tcttgggaca gaatggaatc      900
tcagacgttg tgaaagtgac tctgactcat gaagaagagg cctgtttgaa gaagagtgca     960 gatacactt gggggatcca gaaagaactg cagttttaa                              999
```

```
<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctcgagatgg caactctaaa ggatca                                            26
```

```
<210> SEQ ID NO 5
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 5
gcggccgctt aaaattgcag ctcctttt                                          28

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtcgacatgg caactgtgaa ggataa                                            26

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gcggccgcct agaactgcag ctcctt                                            26

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctcgagatgg caactctcaa ggatca                                            26

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcggccgctt aaaactgcag ttctttct                                          28

<210> SEQ ID NO 10
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
accgttttcg gtttgccagg tgacttcaac ttgtccttgt tggacagatt gtactgagag       60
tgcac                                                                   65

<210> SEQ ID NO 11
<211> LENGTH: 65
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 11
atcgaagact ggcaacatga tttcaatcat tctgatctta gagttctgtg cggtatttca    60
caccg                                                                65

<210> SEQ ID NO 12
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
accgttttcg gtttgccagg tgacttcaac ttgtccttgt tggacagatt gtactgagag    60
tgcac                                                                65

<210> SEQ ID NO 13
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
atcgaagact ggcaacatga tttcaatcat tctgatctta gagttctgtg cggtatttca    60
caccg                                                                65

<210> SEQ ID NO 14
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tctcaattat tattttctac tcataacctc acgcaaaata acacagtcaa atcaatcaaa    60
atggcaactc taaaggatca gctga                                          85

<210> SEQ ID NO 15
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tctcaattat tattttctac tcataacctc acgcaaaata acacagtcaa atcaatcaaa    60
atggcaactg tgaaggataa actca                                          85

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
```
aggcgtatca cgaggccctt                                          20

<210> SEQ ID NO 17
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tctcaattat tattttctac tcataacctc acgcaaaata acacagtcaa atcaatcaaa   60

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gaattaattc ttgaagacga aagggcctcg tgatacgcct agattgtact gagagtgcac   60

<210> SEQ ID NO 19
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19 tattttcgt tacataaaaa tgcttataaa actttaacta ataattagag attaaatcgc    60
ctgtgcggta tttcacaccg                                              80

<210> SEQ ID NO 20
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20 tattttcgt tacataaaaa tgcttataaa actttaacta ataattagag attaaatcgc    60

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
caaatatcgt ttgaatattt ttccg                                        25

<210> SEQ ID NO 22
<211> LENGTH: 1602
<212> TYPE: DNA
<213> ORGANISM: Saccharomyces cerevisiae

<400> SEQUENCE: 22
atgaagtaca tggtagtcag ctcgcctata caagaggttt taagattaca taaatatatt   60

-continued

```
gagatctcta ctaccacaat cacagttaaa attacaaata agatgtcctc tccagtgatt     120
ggtatcacct ttggtaacac ctcttcttct attgcctaca tcaacccaaa gaacgatgtt     180
gatgtcattg ccaacccaga tggtgagcgt gccattccat ccgctttatc ctatgtcggt     240
gaagatgaat accacggtgg tcaagctttg caacaattaa tcagaaatcc taagaatact     300
atcattaact tccgtgactt cattggtttg ccatttgaca agtgtgatgt cagcaagtgc     360
gctaacggtg ccccagctgt cgaagttgat ggcaaagttg gatttgttat ttcaagaggc     420
gaaggtaagg aagaaaaact tactgtagat gaagtggtct ccagacattt aaacagatta     480
aagttagccg cggaagatta catcggttct gccgtaaagg aagctgtatt gacagttcca     540
acaaacttca gtgaagaaca aaagactgca ctaaaggctt ctgccgccaa aattggtctg     600
caaattgttc aattcatcaa tgaaccttct gctgctttat tagcccacgc tgaacaattc     660
ccatttgaaa aagatgttaa cgttgttgtt gctgacttcg gtggtattag atctgacgct     720
gctgtcattg ccgttcgtaa cggtattttc actattttgg ccactgctca tgacctcagc     780
ttaggtggtg acaatttgga tactgaatta gtcgaatatt ttgctagtga gttccaaaag     840
aagtatcaag ccaatccaag aaagaacgct agatccttgg ccaagttaaa ggctaactct     900
tcaattacca agaagacttt gtccaacgca acttctgcca ctatttccat cgattcctta     960
gctgatggtt tcgactatca cgcttctatc aacagaatga ggtacgaatt ggtagctaac    1020
aaggtcttcg cccaattttc ctctttcgtt gattctgtca ttgccaaggc tgaattagac    1080
ccattggaca tcgatgctgt tcttttgact ggtggtgtat catttactcc aaaattaacc    1140
actaacttgg aatacacttt accagaatca gtcgaaattc ttggtccaca gaacaagaac    1200
gcttctaaca atccaaacga attagctgca tccggtgccg cattacaagc aagattgatt    1260
agcgattacg atgctgacga attggctgaa gctttacaac cagttatcgt caatactcca    1320
catttaaaga agcctattgg tttgattggt gctaagggcg aattccaccc agtattgttg    1380
gctgaaactt cgttccctgt acaaaagaaa ttgactttga acaagccaa gggtgatttc    1440 ttgattggtg tttacgaagg tgaccatcac atcgaggaaa agactttgga gccaattcca    1500
aaagaagaaa atgctgaaga ggacgatgaa agtgaatggt ccgacgatga acctgaagtc    1560
gtcagagaaa aactatacac tttgggtacc aagttgatgt aa                       1602
```

<210> SEQ ID NO 23
<211> LENGTH: 533
<212> TYPE: PRT
<213> ORGANISM: Saccharomyces cerevisiae

<400> SEQUENCE: 23

```
Met Lys Tyr Met Val Val Ser Ser Pro Ile Gln Glu Val Leu Arg Leu
1               5                   10                  15

His Lys Tyr Ile Glu Ile Ser Thr Thr Thr Ile Thr Val Lys Ile Thr
            20                  25                  30

Asn Lys Met Ser Ser Pro Val Ile Gly Ile Thr Phe Gly Asn Thr Ser
        35                  40                  45

Ser Ser Ile Ala Tyr Ile Asn Pro Lys Asn Asp Val Asp Val Ile Ala
    50                  55                  60

Asn Pro Asp Gly Glu Arg Ala Ile Pro Ser Ala Leu Ser Tyr Val Gly
65                  70                  75                  80

Glu Asp Glu Tyr His Gly Gly Gln Ala Leu Gln Gln Leu Ile Arg Asn
                85                  90                  95

Pro Lys Asn Thr Ile Ile Asn Phe Arg Asp Phe Ile Gly Leu Pro Phe
            100                 105                 110
```

```
Asp Lys Cys Asp Val Ser Lys Cys Ala Asn Gly Ala Pro Ala Val Glu
        115                 120                 125
Val Asp Gly Lys Val Gly Phe Val Ile Ser Arg Gly Glu Gly Lys Glu
130                 135                 140
Glu Lys Leu Thr Val Asp Glu Val Val Ser Arg His Leu Asn Arg Leu
145                 150                 155                 160
Lys Leu Ala Ala Glu Asp Tyr Ile Gly Ser Ala Val Lys Glu Ala Val
                165                 170                 175
Leu Thr Val Pro Thr Asn Phe Ser Glu Glu Gln Lys Thr Ala Leu Lys
            180                 185                 190
Ala Ser Ala Ala Lys Ile Gly Leu Gln Ile Val Gln Phe Ile Asn Glu
        195                 200                 205
Pro Ser Ala Ala Leu Leu Ala His Ala Glu Gln Phe Pro Phe Glu Lys
    210                 215                 220
Asp Val Asn Val Val Ala Asp Phe Gly Gly Ile Arg Ser Asp Ala
225                 230                 235                 240
Ala Val Ile Ala Val Arg Asn Gly Ile Phe Thr Ile Leu Ala Thr Ala
                245                 250                 255
His Asp Leu Ser Leu Gly Gly Asp Asn Leu Asp Thr Glu Leu Val Glu
            260                 265                 270
Tyr Phe Ala Ser Glu Phe Gln Lys Lys Tyr Gln Ala Asn Pro Arg Lys
        275                 280                 285
Asn Ala Arg Ser Leu Ala Lys Leu Lys Ala Asn Ser Ser Ile Thr Lys
    290                 295                 300
Lys Thr Leu Ser Asn Ala Thr Ser Ala Thr Ile Ser Ile Asp Ser Leu
305                 310                 315                 320
Ala Asp Gly Phe Asp Tyr His Ala Ser Ile Asn Arg Met Arg Tyr Glu
                325                 330                 335
Leu Val Ala Asn Lys Val Phe Ala Gln Phe Ser Ser Phe Val Asp Ser
            340                 345                 350
Val Ile Ala Lys Ala Glu Leu Asp Pro Leu Asp Ile Asp Ala Val Leu
        355                 360                 365
Leu Thr Gly Gly Val Ser Phe Thr Pro Lys Leu Thr Thr Asn Leu Glu
    370                 375                 380
Tyr Thr Leu Pro Glu Ser Val Glu Ile Leu Gly Pro Gln Asn Lys Asn
385                 390                 395                 400
Ala Ser Asn Asn Pro Asn Glu Leu Ala Ala Ser Gly Ala Ala Leu Gln
                405                 410                 415
Ala Arg Leu Ile Ser Asp Tyr Asp Ala Asp Glu Leu Ala Glu Ala Leu
            420                 425                 430
Gln Pro Val Ile Val Asn Thr Pro His Leu Lys Lys Pro Ile Gly Leu
        435                 440                 445
Ile Gly Ala Lys Gly Glu Phe His Pro Val Leu Leu Ala Glu Thr Ser
    450                 455                 460
Phe Pro Val Gln Lys Lys Leu Thr Leu Lys Gln Ala Lys Gly Asp Phe
465                 470                 475                 480
Leu Ile Gly Val Tyr Glu Gly Asp His His Ile Glu Lys Thr Leu
                485                 490                 495
Glu Pro Ile Pro Lys Glu Glu Asn Ala Glu Glu Asp Asp Glu Ser Glu
            500                 505                 510
Trp Ser Asp Asp Glu Pro Glu Val Val Arg Glu Lys Leu Tyr Thr Leu
        515                 520                 525
Gly Thr Lys Leu Met
```

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
atgcggtacc gtgatgaggc tcgtggaaaa                                30

<210> SEQ ID NO 25
<211> LENGTH: 66
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
tgcttataaa actttaacta ataattagag attaaatcgc gatatctttg attgatttga     60
ctgtgt                                                               66

<210> SEQ ID NO 26
<211> LENGTH: 530
<212> TYPE: DNA
<213> ORGANISM: Saccharomyces cerevisiae

<400> SEQUENCE: 26
atgcggtacc gtgatgaggc tcgtggaaaa aatgaataat ttatgaattt gagaacaatt     60
ttgtgttgtt acggtatttt actatggaat aatcaatcaa ttgaggattt tatgcaaata    120
tcgtttgaat atttttccga ccctttgagt acttttcttc ataattgcat aatattgtcc    180
gctgccccct tttctgttag acggtgtctt gatctacttg ctatcgttca acaccacctt    240
attttctaac tattttttttt ttagctcatt tgaatcagct tatggtgatg gcacattttt    300
gcataaacct agctgtcctc gttgaacata ggaaaaaaaa atatataaac aaggctcttt    360
cactctcctt gcaatcagat ttgggtttgt tccctttatt ttcatatttc ttgtcatatt    420
cctttctcaa ttattatttt ctactcataa cctcacgcaa aataacacag tcaaatcaat    480
caaagatatc gcgatttaat ctctaattat tagttaaagt tttataagca                530

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
gatatcgcga tttaatctct aattattagt                                30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 28

```
atgcggtacc gcaccaagtg gcgtagaaat                                      30
```

<210> SEQ ID NO 29
<211> LENGTH: 482
<212> TYPE: DNA
<213> ORGANISM: Saccharomyces cerevisiae

<400> SEQUENCE: 29

```
gatatcgcga tttaatctct aattattagt taaagtttta taagcatttt tatgtaacga     60
aaaataaatt ggttcatatt attactgcac tgtcacttac catggaaaga ccagacaaga    120
agttgccgac agtctgttga attggcctgg ttaggcttaa gtctgggtcc gcttctttac    180
aaatttggag aatttctctt aaacgatatg tatattcttt tcgttggaaa agatgtcttc    240
caaaaaaaaa accgatgaat tagtggaacc aaggaaaaaa aaagaggtat ccttgattaa    300
ggaacactgt ttaaacagtg tggtttccaa acccctgaaa ctgcattagt gtaatagaag    360
actagacacc tcgatacaaa taatggttac tcaattcaaa actgccagcg aattcgactc    420
tgcaattgct caagacaagc tagttgtcgt agatttctac gccacttggt gcggtaccgc    480
at                                                                  482
```

<210> SEQ ID NO 30
<211> LENGTH: 966
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30

```
atgcggtacc gtgatgaggc tcgtggaaaa aatgaataat ttatgaattt gagaacaatt     60
ttgtgttgtt acggtatttt actatggaat aatcaatcaa ttgaggattt tatgcaaata    120
tcgtttgaat atttttccga ccctttgagt acttttcttc ataattgcat aatattgtcc    180
gctgccccctt tttctgttag acggtgtctt gatctacttg ctatcgttca acaccacctt    240
attttctaac tatttttttt ttagctcatt tgaatcagct tatggtgatg gcacattttt    300
gcataaacct agctgtcctc gttgaacata ggaaaaaaaa atatataaac aaggctcttt    360
cactctcctt gcaatcagat ttgggtttgt tccctttatt ttcatatttc ttgtcatatt    420
cctttctcaa ttattatttt ctactcataa cctcacgcaa aataacacag tcaaatcaat    480
caaagatatc gcgatttaat ctctaattat tagttaaagt tttataagca tttttatgta    540
acgaaaaata aattggttca tattattact gcactgtcac ttaccatgga agaccagac    600
aagaagttgc cgacagtctg ttgaattggc ctggttaggc ttaagtctgg gtccgcttct    660
ttacaaattt ggagaatttc tcttaaacga tatgtatatt cttttcgttg aaaagatgt    720
cttccaaaaa aaaaccgat gaattagtgg aaccaaggaa aaaaaagag gtatccttga    780
ttaaggaaca ctgtttaaac agtgtggttt ccaaaacccct gaaactgcat tagtgtaata    840
gaagactaga cacctcgata caaataatgg ttactcaatt caaaactgcc agcgaattcg    900
actctgcaat tgctcaagac aagctagttg tcgtagattt ctacgccact tggtgcggta    960
ccgcat                                                              966
```

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
gaagggacaa ccaggacgta                                          20

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
agcccaactg aaaggttgc                                           19

<210> SEQ ID NO 33
<211> LENGTH: 83
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tccgacgatg aacctgaagt cgtcagagaa aaactataca ctttgggtac caagttgatg    60
tagagattgt actgagagtg cac                                           83

<210> SEQ ID NO 34
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
accgtctttg ttaatgttaa agataatttc aacaccgtta gcgttttaa ttcccaattc    60 ctgtgcggta tttcacaccg                                              80

<210> SEQ ID NO 35
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tccgacgatg aacctgaagt cgtcagagaa aaactataca ctttgggtac caagttgatg    60
tag                                                                63

<210> SEQ ID NO 36
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gaattgggaa ttaaaaacgc taacggtgtt gaaattatct ttaacattaa caaagacggt    60

<210> SEQ ID NO 37
<211> LENGTH: 80

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tagttccatc atgtatgtat ttttctatat acgtatacat accgtttttc ttagagcgct    60
ctgtgcggta tttcacaccg                                                80

<210> SEQ ID NO 38
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
agcgctctaa gaaaaacggt atgtatacgt atatagaaaa atacatacat gatggaacta   60

<210> SEQ ID NO 39
<211> LENGTH: 348
<212> TYPE: PRT
<213> ORGANISM: Saccharomyces cerevisiae

<400> SEQUENCE: 39
```

| Met | Ser | Ile | Pro | Glu | Thr | Gln | Lys | Gly | Val | Ile | Phe | Tyr | Glu | Ser | His |
|---|---|---|---|---|---|---|---|---|---|---|---|---|---|---|---|
| 1 | | | | 5 | | | | | 10 | | | | | 15 | |

| Gly | Lys | Leu | Glu | Tyr | Lys | Asp | Ile | Pro | Val | Pro | Lys | Pro | Lys | Ala | Asn |
|---|---|---|---|---|---|---|---|---|---|---|---|---|---|---|---|
| | | | 20 | | | | | 25 | | | | | 30 | | |

| Glu | Leu | Leu | Ile | Asn | Val | Lys | Tyr | Ser | Gly | Val | Cys | His | Thr | Asp | Leu |
|---|---|---|---|---|---|---|---|---|---|---|---|---|---|---|---|
| | | 35 | | | | | 40 | | | | | 45 | | | |

| His | Ala | Trp | His | Gly | Asp | Trp | Pro | Leu | Pro | Val | Lys | Leu | Pro | Leu | Val |
|---|---|---|---|---|---|---|---|---|---|---|---|---|---|---|---|
| | 50 | | | | | 55 | | | | | 60 | | | | |

| Gly | Gly | His | Glu | Gly | Ala | Gly | Val | Val | Val | Gly | Met | Gly | Glu | Asn | Val |
|---|---|---|---|---|---|---|---|---|---|---|---|---|---|---|---|
| 65 | | | | | 70 | | | | | 75 | | | | | 80 |

| Lys | Gly | Trp | Lys | Ile | Gly | Asp | Tyr | Ala | Gly | Ile | Lys | Trp | Leu | Asn | Gly |
|---|---|---|---|---|---|---|---|---|---|---|---|---|---|---|---|
| | | | 85 | | | | | 90 | | | | | 95 | | |

| Ser | Cys | Met | Ala | Cys | Glu | Tyr | Cys | Glu | Leu | Gly | Asn | Glu | Ser | Asn | Cys |
|---|---|---|---|---|---|---|---|---|---|---|---|---|---|---|---|
| | | | 100 | | | | | 105 | | | | | 110 | | |

| Pro | His | Ala | Asp | Leu | Ser | Gly | Tyr | Thr | His | Asp | Gly | Ser | Phe | Gln | Gln |
|---|---|---|---|---|---|---|---|---|---|---|---|---|---|---|---|
| | | 115 | | | | | 120 | | | | | 125 | | | |

| Tyr | Ala | Thr | Ala | Asp | Ala | Val | Gln | Ala | Ala | His | Ile | Pro | Gln | Gly | Thr |
|---|---|---|---|---|---|---|---|---|---|---|---|---|---|---|---|
| | 130 | | | | | 135 | | | | | 140 | | | | |

| Asp | Leu | Ala | Gln | Val | Ala | Pro | Ile | Leu | Cys | Ala | Gly | Ile | Thr | Val | Tyr |
|---|---|---|---|---|---|---|---|---|---|---|---|---|---|---|---|
| 145 | | | | | 150 | | | | | 155 | | | | | 160 |

| Lys | Ala | Leu | Lys | Ser | Ala | Asn | Leu | Met | Ala | Gly | His | Trp | Val | Ala | Ile |
|---|---|---|---|---|---|---|---|---|---|---|---|---|---|---|---|
| | | | 165 | | | | | 170 | | | | | 175 | | |

| Ser | Gly | Ala | Ala | Gly | Gly | Leu | Gly | Ser | Leu | Ala | Val | Gln | Tyr | Ala | Lys |
|---|---|---|---|---|---|---|---|---|---|---|---|---|---|---|---|
| | | | 180 | | | | | 185 | | | | | 190 | | |

| Ala | Met | Gly | Tyr | Arg | Val | Leu | Gly | Ile | Asp | Gly | Gly | Glu | Gly | Lys | Glu |
|---|---|---|---|---|---|---|---|---|---|---|---|---|---|---|---|
| | | 195 | | | | | 200 | | | | | 205 | | | |

| Glu | Leu | Phe | Arg | Ser | Ile | Gly | Gly | Glu | Val | Phe | Ile | Asp | Phe | Thr | Lys |
|---|---|---|---|---|---|---|---|---|---|---|---|---|---|---|---|
| | 210 | | | | | 215 | | | | | 220 | | | | |

| Glu | Lys | Asp | Ile | Val | Gly | Ala | Val | Leu | Lys | Ala | Thr | Asp | Gly | Gly | Ala |
|---|---|---|---|---|---|---|---|---|---|---|---|---|---|---|---|
| 225 | | | | | 230 | | | | | 235 | | | | | 240 |

| His | Gly | Val | Ile | Asn | Val | Ser | Val | Ser | Glu | Ala | Ala | Ile | Glu | Ala | Ser |
|---|---|---|---|---|---|---|---|---|---|---|---|---|---|---|---|
| | | | 245 | | | | | 250 | | | | | 255 | | |

```
Thr Arg Tyr Val Arg Ala Asn Gly Thr Thr Val Leu Val Gly Met Pro
            260                 265                 270

Ala Gly Ala Lys Cys Cys Ser Asp Val Phe Asn Gln Val Val Lys Ser
            275                 280                 285

Ile Ser Ile Val Gly Ser Tyr Val Gly Asn Arg Ala Asp Thr Arg Glu
            290                 295                 300

Ala Leu Asp Phe Phe Ala Arg Gly Leu Val Lys Ser Pro Ile Lys Val
305                 310                 315                 320

Val Gly Leu Ser Thr Leu Pro Glu Ile Tyr Glu Lys Met Glu Lys Gly
            325                 330                 335

Gln Ile Val Gly Arg Tyr Val Val Asp Thr Ser Lys
            340                 345

<210> SEQ ID NO 40
<211> LENGTH: 348
<212> TYPE: PRT
<213> ORGANISM: Saccharomyces cerevisiae

<400> SEQUENCE: 40

Met Ser Ile Pro Glu Thr Gln Lys Gly Val Ile Phe Tyr Glu Ser His
1               5                   10                  15

Gly Lys Leu Glu Tyr Lys Asp Ile Pro Val Pro Lys Pro Lys Ala Asn
            20                  25                  30

Glu Leu Leu Ile Asn Val Lys Tyr Ser Gly Val Cys His Thr Asp Leu
        35                  40                  45

His Ala Trp His Gly Asp Trp Pro Leu Pro Val Lys Leu Pro Leu Val
    50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Gln
        115                 120                 125

Tyr Ala Thr Ala Asp Ala Val Gln Ala Ala His Thr Pro Gln Gly Thr
    130                 135                 140

Asp Leu Ala Gln Val Ala Pro Ile Leu Cys Ala Gly Ile Thr Val Tyr
145                 150                 155                 160

Lys Ala Leu Lys Ser Ala Asn Leu Met Ala Gly His Trp Val Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Glu Gly Lys Glu
        195                 200                 205

Glu Leu Phe Arg Ser Ile Gly Gly Glu Val Phe Ile Asp Phe Thr Lys
    210                 215                 220

Glu Lys Asp Ile Val Gly Ala Val Leu Lys Ala Thr Asp Gly Gly Ala
225                 230                 235                 240

His Gly Val Ile Asn Val Ser Val Ser Glu Ala Ala Ile Glu Ala Ser
                245                 250                 255

Thr Arg Tyr Val Arg Ala Asn Gly Thr Thr Val Leu Val Gly Met Pro
            260                 265                 270

Ala Gly Ala Lys Cys Cys Ser Asp Val Phe Asn Gln Ala Val Lys Ser
            275                 280                 285
```

```
Ile Ser Ile Val Gly Ser Tyr Val Gly Asn Arg Ala Asp Thr Arg Glu
    290                 295                 300

Ala Leu Asp Phe Phe Ala Arg Gly Leu Val Lys Ser Pro Ile Lys Val
305                 310                 315                 320

Val Gly Leu Ser Thr Leu Pro Glu Ile Tyr Glu Lys Met Glu Lys Gly
                325                 330                 335

Gln Ile Val Gly Arg Tyr Val Val Asp Thr Ser Lys
            340                 345

<210> SEQ ID NO 41
<211> LENGTH: 348
<212> TYPE: PRT
<213> ORGANISM: Saccharomyces cerevisiae

<400> SEQUENCE: 41

Met Ser Ile Pro Glu Thr Gln Lys Gly Val Ile Phe Tyr Glu Ser His
1               5                   10                  15

Gly Lys Leu Glu Tyr Lys Asp Ile Pro Val Pro Lys Pro Lys Ala Asn
            20                  25                  30

Glu Leu Leu Ile Asn Val Lys Tyr Ser Gly Val Cys His Thr Asp Leu
        35                  40                  45

His Ala Trp His Gly Asp Trp Pro Leu Pro Val Lys Leu Pro Leu Val
    50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Gln
        115                 120                 125

Tyr Ala Thr Ala Asp Ala Val Gln Ala Ala His Ile Pro Gln Gly Thr
    130                 135                 140

Asp Leu Ala Gln Val Ala Pro Ile Leu Cys Ala Gly Ile Thr Val Tyr
145                 150                 155                 160

Lys Ala Leu Lys Pro Ala Asn Leu Met Ala Gly His Trp Val Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Glu Gly Lys Glu
        195                 200                 205

Glu Leu Phe Arg Ser Ile Gly Gly Glu Val Phe Ile Asp Phe Thr Lys
    210                 215                 220

Glu Lys Asp Ile Val Gly Ala Val Leu Lys Ala Thr Asp Gly Gly Ala
225                 230                 235                 240

His Gly Val Ile Asn Val Ser Val Ser Glu Ala Ala Ile Glu Ala Ser
                245                 250                 255

Thr Arg Tyr Val Arg Ala Asn Gly Thr Thr Val Leu Val Gly Met Pro
            260                 265                 270

Ala Gly Ala Lys Cys Cys Ser Asp Val Phe Asn Gln Ala Val Lys Ser
        275                 280                 285

Ile Ser Ile Val Gly Ser Tyr Val Gly Asn Arg Ala Asp Thr Arg Glu
    290                 295                 300

Ala Leu Asp Phe Phe Ala Arg Gly Leu Val Lys Ser Pro Ile Lys Val
305                 310                 315                 320
```

Val Gly Leu Ser Thr Leu Pro Glu Ile Tyr Glu Lys Met Lys Gly
            325                 330                 335

Gln Ile Val Gly Arg Tyr Val Val Asp Thr Ser Lys
            340                 345

<210> SEQ ID NO 42
<211> LENGTH: 348
<212> TYPE: PRT
<213> ORGANISM: Saccharomyces cerevisiae

<400> SEQUENCE: 42

Met Ser Ile Pro Glu Thr Gln Lys Gly Val Ile Phe Tyr Glu Ser His
1               5                   10                  15

Gly Lys Leu Glu Tyr Lys Asp Ile Pro Val Pro Lys Pro Lys Ala Asn
            20                  25                  30

Glu Leu Leu Ile Asn Val Lys Tyr Ser Gly Val Cys His Thr Asp Leu
        35                  40                  45

His Ala Trp His Gly Asp Trp Pro Leu Pro Val Lys Leu Pro Leu Val
    50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Gln
        115                 120                 125

Tyr Ala Thr Ala Asp Ala Val Gln Ala Ala His Ile Pro Gln Gly Thr
    130                 135                 140

Asp Leu Ala Gln Val Ala Pro Ile Leu Cys Ala Gly Ile Thr Val Tyr
145                 150                 155                 160

Lys Ala Leu Lys Ser Ala Asn Leu Met Ala Gly His Trp Val Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Glu Gly Lys Glu
        195                 200                 205

Glu Leu Phe Arg Ser Ile Gly Gly Glu Val Phe Ile Asp Phe Thr Lys
    210                 215                 220

Glu Lys Asp Ile Val Gly Ala Val Leu Lys Ala Thr Asp Gly Gly Ala
225                 230                 235                 240

His Gly Val Ile Asn Val Ser Val Ser Glu Ala Ala Ile Glu Ala Ser
                245                 250                 255

Thr Arg Tyr Val Arg Ala Asn Gly Thr Thr Val Leu Val Gly Met Pro
            260                 265                 270

Ala Gly Ala Lys Cys Cys Ser Asp Val Phe Asn Gln Ala Val Lys Ser
        275                 280                 285

Ile Ser Ile Val Gly Ser Tyr Val Gly Asn Arg Ala Asp Thr Arg Glu
    290                 295                 300

Ala Leu Asp Phe Phe Ala Arg Gly Leu Val Lys Ser Pro Ile Lys Val
305                 310                 315                 320

Val Gly Leu Ser Thr Leu Pro Glu Ile Tyr Glu Lys Met Glu Lys Gly
                325                 330                 335

Gln Ile Val Gly Arg Tyr Val Val Asp Thr Ser Lys
            340                 345

<210> SEQ ID NO 43
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gcacaatatt tcaagctata ccaagcatac aatcaactat ctcatataca atgtcgaaag    60
ctacatataa                                                          70

<210> SEQ ID NO 44
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
atttttttta taacttattt aataataaaa atcataaatc ataagaaatt ttagttttgc    60
tggccgcatc                                                          70

<210> SEQ ID NO 45
<211> LENGTH: 50
<212> TYPE: DNA
<213> ORGANISM: Saccharomyces cerevisiae

<400> SEQUENCE: 45
gcacaatatt tcaagctata ccaagcatac aatcaactat ctcatataca              50

<210> SEQ ID NO 46
<211> LENGTH: 53
<212> TYPE: DNA
<213> ORGANISM: Saccharomyces cerevisiae

<400> SEQUENCE: 46
taaaatttct tatgatttat gattttatt attaaataag ttataaaaaa aat           53

<210> SEQ ID NO 47
<211> LENGTH: 30
<212> TYPE: DNA
<213> ORGANISM: Saccharomyces cerevisiae

<400> SEQUENCE: 47
gggtgtacaa tatggacttc ctcttttctg                                    30

<210> SEQ ID NO 48
<211> LENGTH: 30
<212> TYPE: DNA
<213> ORGANISM: Saccharomyces cerevisiae

<400> SEQUENCE: 48
catttgctcg gcatgccggt agaggtgtgg                                    30

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 49
atgtctatcc cagaaactca aaaag                                          25

<210> SEQ ID NO 50
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ttatttagaa gtgtcaacaa cgtatct                                        27

<210> SEQ ID NO 51
<211> LENGTH: 1692
<212> TYPE: DNA
<213> ORGANISM: Saccharomyces cerevisiae

<400> SEQUENCE: 51
atgtctgaaa taaccttagg taaatatttta tttgaaagat tgagccaagt caactgtaac    60
accgtcttcg gtttgccagg tgactttaac ttgtctcttt tggataagct ttatgaagtc   120
aaaggtatga gatgggctgg taacgctaac gaattgaacg ctgcctatgc tgctgatggt   180
tacgctcgta tcaagggtat gtcctgtatt attaccacct tcggtgttgg tgaattgtct   240
gctttgaatg gtattgccgg ttcttacgct gaacatgtcg gtgttttgca cgttgttggt   300
gttccatcca tctcttctca agctaagcaa ttgttgttgc atcataccct gggtaacggt   360
gacttcactg tttccacag aatgtctgcc aacatttctg aaaccactgc catgatcact   420
gatattgcta acgctccagc tgaaattgac agatgtatca gaaccaccta cactacccaa   480
agaccagtct acttgggttt gccagctaac ttggttgact gaacgtccc agccaagtta   540 ttggaaactc caattgactt gtctttgaag ccaaacgacg ctgaagctga agctgaagtt   600
gttagaactg ttgttgaatt gatcaaggat gctaagaacc cagttatctt ggctgatgct   660
tgtgcttcta cactgatgt caaggctgaa actaagaagt tgatggactt gactcaattc   720
ccagtttacg tcacccccaat gggtaagggt gctattgacg aacaacaccc aagatacggt   780
ggtgtttacg ttggtacctt gtctagacca gaagttaaga aggctgtaga atctgctgat   840
ttgatattgt ctatcggtgc tttgttgtct gatttcaata ccggttcttt ctcttactcc   900
tacaagacca aaatatcgt tgaattccac tctgaccaca tcaagatcag aaacgccacc   960
ttcccaggtg ttcaaatgaa atttgccttg caaaaattgt tggatgctat tccagaagtc  1020
gtcaaggact acaaacctgt tgctgtccca gctagagttc aattaccaa gtctactcca  1080 gctaacactc caatgaagca agaatggatg tggaaccatt tgggtaactt cttgagagaa  1140
ggtgatattg ttattgctga aaccggtact tccgccttcg gtattaacca aactactttc  1200
ccaacagatg tatacgctat cgtccaagtc ttgtggggtt ccattggttt cacagtcggc  1260
gctctattgg gtgctactat ggccgctgaa gaacttgatc aaagaagag agttatttta  1320 ttcattggtg acggttctct acaattgact gttcaagaaa tctctaccat gattagatgg  1380 ggttttgaagc catacatttt tgtcttgaat aacaacggtt acaccattga aaaattgatt  1440
cacggtcctc atgccgaata taatgaaatt caaggttggg accacttggc cttattgcca  1500
acttttggtg ctagaaacta cgaaaccccac agagttgcta ccactggtga atgggaaaag  1560
ttgactcaag acaaggactt ccaagacaac tctaagatta gaatgattga agttatgttg  1620
ccagtctttg atgctccaca aaacttggtt aaacaagctc aattgactgc cgctactaac  1680
```
gctaaacaat aa                                                                         1692

<210> SEQ ID NO 52
<211> LENGTH: 1692
<212> TYPE: DNA
<213> ORGANISM: Saccharomyces cerevisiae

<400> SEQUENCE: 52

```
atgtctgaaa taaccttagg taaatattta tttgaaagat tgagccaagt caactgtaac      60
accgtcttcg gtttgccagg tgactttaac ttgtctcttt tggataagct ttatgaagtc     120
aaaggtatga gatgggctgg taacgctaac gaattgaacg ctgcctatgc tgctgatggt     180
tacgctcgta tcaagggtat gtcctgtatt attaccacct tcggtgttgg tgaattgtct     240
gctttgaatg gtattgccgg ttcttacgct gaacatgtcg gtgttttgca cgttgttggt     300
gttccatcca tctcttctca agctaagcaa ttgttgttgc atcataccct gggtaacggt     360
gacttcactg ttttccacag aatgtctgcc aacatttctg aaaccactgc catgatcact     420
gatattgcta acgctccagc tgaaattgac agatgtatca gaaccaccta cactacccaa     480
agaccagtct acttgggttt gccagctaac ttggttgact gaacgtccc agccaagtta     540
ttggaaactc aattgactt gtctttgaag ccaaacgacg ctgaagctga agctgaagtt     600
gttagaactg ttgttgaatt gatcaaggat gctaagaacc cagttatctt ggctgatgct     660
tgtgcttcta gacatgatgt caaggctgaa actaagaagt gatggactt gactcaattc     720
ccagtttacg tcaccccaat gggtaagggt gctattgacg aacaaacccc aagatacggt     780
ggtgtttacg ttggtacctt gtctagacca gaagttaaga aggctgtaga atctgctgat     840
tgatattgt ctatcggtgc tttgttgtct gatttcaata ccggttcttt ctcttactcc     900
tacaagacca aaaatatcgt tgaattccac tctgaccaca tcaagatcag aaacgccacc     960
ttcccaggtg ttcaaatgaa atttgccttg caaaaattgt tggatgctat tccagaagtc    1020
gtcaaggact acaaacctgt tgctgtccca gctagagttc aattaccaa gtctactcca    1080
gctaacactc caatgaagca agaatggatg tggaaccatt tgggtaactt cttgagagaa    1140
ggtgatattg ttattgctga aaccggtact tccgccttcg gtattaacca aactactttc    1200
ccaacagatg tatacgctat cgtccaagtc ttgtgggggtt ccattggttt cacagtcggc    1260
gctctattgg gtgctactat ggccgctgaa gaacttgatc aaagaagag agttattta     1320
ttcattggtg acggttctct acaattgact gttcaagaaa tctctaccat gattagatgg    1380
ggtttgaagc catacatttt tgtcttgaat aacaacggtt acaccattga aaaattgatt    1440
cacggtcctc atgccgaata taatgaaatt caaggttggg accacttggc cttattgcca    1500
acttttggtg ctagaaacta cgaaacccac agagttgcta ccactggtga atgggaaaag    1560
ttgactcaag acaaggactt ccaagacaac tctaagatta gaatgattga agttatgttg    1620
ccagtctttg atgctccaca aaacttggtt aaacaagctc aattgactgc cgctactaac    1680
gctaaacaat aa                                                         1692
```

<210> SEQ ID NO 53
<211> LENGTH: 1692
<212> TYPE: DNA
<213> ORGANISM: Saccharomyces cerevisiae

<400> SEQUENCE: 53

```
atgtctgaaa taaccttagg taaatattta tttgaaagat tgagccaagt caactgtaac      60
accgtcttcg gtttgccagg tgactttaac ttgtctcttt tggataagct ttatgaagtc     120
```

```
aaaggtatga gatgggctgg taacgctaac gaattgaacg ctgcctatgc tgctgatggt    180
tacgctcgta tcaagggtat gtcctgtatt attaccacct tcggtgttgg tgaattgtct    240
gctttgaatg gtattgccgg ttcttacgct gaacatgtcg gtgttttgca cgttgttggt    300
gttccatcca tctcttctca agctaagcaa ttgttgttgc atcataccct gggtaacggt    360
gacttcactg ttttccacag aatgtctgcc aacatttctg aaaccactgc catgatcact    420
gatattgcta acgctccagc tgaaattgac agatgtatca gaaccaccta cactacccaa    480
agaccagtct acttgggttt gccagctaac ttggttgact gaacgtccc agccaagtta    540 ttggaaactc aattgacttt gtctttgaag ccaaacgacg ctgaagctga agctgaagtt    600
gttagaactg ttgttgaatt gatcaaggat gctaagaacc cagttatctt ggctgatgct    660
tgtgcttcta gacatgatgt caaggctgaa actaagaagt tgatggactt gactcaattc    720
ccagtttacg tcaccccaat gggtaagggt gctattgacg aacaacaccc aagatacggt    780
ggtgtttacg ttggtacctt gtctagacca gaagttaaga aggctgtaga atctgctgat    840
ttgatattgt ctatcggtgc tttgttgtct gatttcaata ccggttcttt ctcttactcc    900
tacaagacca aaaatatcgt tgaattccac tctgaccaca tcaagatcag aaacgccacc    960
ttcccaggtg ttcaaatgaa atttgccttg caaaaattgt tggatgctat tccagaagtc    1020
gtcaaggact acaaacctgt tgctgtccca gctagagttc aattaccaa gtctactcca    1080 gctaacactc caatgaagca agaatggatg tggaaccatt tgggtaactt cttgagagaa    1140
ggtgatattg ttattgctga aaccggtact tccgccttcg gtattaacca aactactttc    1200
ccaacagatg tatacgctat cgtccaagtc ttgtggggtt ccattggttt cacagtcggc    1260
gctctattgg gtgctactat ggccgctgaa gaacttgatc aaagaagag agttatttta    1320 ttcattggtg acggttctct acaattgact gttcaagaaa tctctaccat gattagatgg    1380
ggtttgaagc catacatttt tgtcttgaat aacaacggtt acaccattga aaaattgatt    1440
cacggtcctc atgccgaata taatgaaatt caaggttggg accacttggc cttattgcca    1500
acttttggtg ctagaaacta cgaaacccac agagttgcta ccactggtga atgggaaaag    1560
ttgactcaag acaaggactt ccaagacaac tctaagatta gaatgattga agttatgttg    1620
ccagtctttg atgctccaca aaacttggtt aaacaagctc aattgactgc cgctactaac    1680
gctaaacaat aa    1692
```

<210> SEQ ID NO 54
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54

```
aatcaatctc aaagagaaca acacaataca ataacaagaa gaacaaaatg agattgtact    60
gagagtgcac                                                           70
```

<210> SEQ ID NO 55
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55

```
gtaaaaaaat acacaaacgt tgaatcatga gttttatgtt aattagctta ctgtgcggta      60
tttcacaccg                                                            70
```

<210> SEQ ID NO 56
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56

```
ctcgatcaat atactgtagt aagtcc                                          26
```

<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57

```
caattattta cctaaacatc tataac                                          26
```

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58

```
caaatatcgt ttgaatattt ttccg                                           25
```

<210> SEQ ID NO 59
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59

```
tacactaatg cagtttcagg gtttt                                           25
```

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60

```
aatgacgacg agcctgaagc tggcg                                           25
```

<210> SEQ ID NO 61
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61

```
ggtaagcagc tgaaagataa taagg                                         25
```

```
<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
atgtctgaaa taaccttagg                                               20
```

```
<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ttattgttta gcgttagtag                                               20
```

```
<210> SEQ ID NO 64
<211> LENGTH: 1716
<212> TYPE: DNA
<213> ORGANISM: Saccharomyces cerevisiae

<400> SEQUENCE: 64
atgaagtaca tggtagtcag ctcgcctata caagaggttt taagattaca taaatatatt    60
gagatctcta ctaccacaat cacagttaaa attacaaata agatgtcctc tccagtgatt   120
ggtatcacct ttggtaacac ctcttcttct attgcctaca tcaacccaaa gaacgatgtt   180
gatgtcattg ccaacccaga tggtgagcgt gccattccat ccgctttatc ctatgtcggt   240
gaagatgaat accacggtgg tcaagctttg caacaattaa tcagaaatcc taagaatact   300
atcattaact tccgtgactt cattggtttg ccatttgaca agtgtgatgt cagcaagtgc   360
gctaacggtg ccccagctgt cgaagttgat ggcaaagttg gatttgttat tcaagaggc    420 gaaggtaagg aagaaaaact tactgtagat gaagtggtct ccagacattt aaacagatta   480
aagttagccg cggaagatta catcggttct gccgtaaagg aagctgtatt gacagttcca   540
acaaacttca gtgaagaaca aaagactgca ctaaaggctt ctgccgccaa aattggtctg   600
caaattgttc aattcatcaa tgaaccttct gctgctttat tagcccacgc tgaacaattc   660
ccatttgaaa aagatgttaa cgttgttgtt gctgacttcg gtggtattag atctgacgct   720
gctgtcattg ccgttcgtaa cggtatttc actattttgg ccactgctca tgacctcagc   780
ttaggtggtg acaatttgga tactgaatta gtcgaatatt ttgctagtga gttccaaaag   840
aagtatcaag ccaatccaag aaagaacgct agatccttgg ccaagttaaa ggctaactct   900
tcaattacca agaagacttt gtccaacgca acttctgcca ctatttccat cgattcctta   960
gctgatggtt tcgactatca cgcttctatc aacagaatga ggtacgaatt ggtagctaac   1020
aaggtcttcg cccaattttc ctctttcgtt gattctgtca ttgccaaggc tgaattagac   1080
ccattggaca tcgatgctgt tctttgact ggtggtgtat catttactcc aaaattaacc   1140
actaacttgg aatacacttt accagaatca gtcgaaattc ttggtccaca gaacaagaac   1200
gcttctaaca atccaaacga attagctgca tccggtgccg cattacaagc aagattgatt   1260
agcgattacg atgctgacga attggctgaa gctttacaac cagttatcgt caatactcca   1320
```

-continued

```
catttaaaga agcctattgg tttgattggt gctaagggcg aattccaccc agtattgttg    1380
gctgaaactt cgttccctgt acaaaagaaa ttgactttga aacaagccaa gggtgatttc    1440
ttgattggtg tttacgaagg tgaccatcac atcgaggaaa agactttgga gccaattcca    1500
aaagaagaaa atgctgaaga ggacgatgaa agtgaatggt ccgacgatga acctgaagtc    1560
gtcagagaaa aactatacac tttgggtacc aagttgatgg aattgggaat taaaaacgct    1620
aacggtgttg aaattatctt taacattaac aaagacggtg ctttaagagt caccgctaga    1680
gatttgaaaa ctggtaatgc tgtaaagggt gaatta                              1716
```

US 8,071,357 B2

YEAST AND METHOD OF PRODUCING L-LACTIC ACID

RELATED APPLICATIONS

This is a §371 of International Application No. PCT/JP2006/317446, with an international filing date of Sep. 4, 2006 (WO 2007/043253 A1, published Apr. 19, 2007), which is based on Japanese Patent Application No. 2005/30415, filed Oct. 14, 2005.

TECHNICAL FIELD

This disclosure relates to methods of producing L-lactic acid and to yeast comprising an introduced gene coding a L-lactate dehydrogenase. The disclosure also relates to methods of producing L-lactic acid comprising culturing the yeast having an introduced gene coding a L-lactate dehydrogenase.

BACKGROUND

In recently increasing interest by society on effective use and reuse of resources, especially polymers produced from plant raw materials are attracting attention. In particular, polylactic acid, a product from a plant-derived raw material, is known recently to have superior properties.

Lactic acid, the raw material for polylactic acid, has been produce by cultivation of a microorganism, generally called lactic bacterium. Typical examples of the lactic bacteria include *Lactobacillus* and *Lactococcus* species. Because these lactic bacteria generally show an excellent yield to sugar, but are less resistant to acid, for accumulation of an acidic substance lactic acid in a great amount, the cultivation should be carried out, while the cultivation solution is neutralized for example with an alkali such as calcium carbonate, ammonium hydroxide or sodium hydroxide.

However, such a process gives a lactate salt such as sodium lactate or calcium lactate by neutralization processing with an alkali, requiring processing to convert the lactate salt back to lactic acid in the later purification step and thus additional cost.

Thus, for reduction of the neutralization cost, lactic acid production by acid-resistant yeast was proposed (see Japanese Patent Application Laid Open (JP-A) No. 2001-204464, JP-A No. 2001-204468, Japanese Patent Application National Publication (Laid-Open) No. 2001-516584, JP-A No. 2003-93060 and JP-A No. 2003-259878 and Danilo Porro et al., Biotechnol. Prog., 11: p. 294-298 (1955), Danilo Porro et al., Applied and Environmental Microbiology, 65 (9): p. 4211-4211 (1999) and Satoshi Saitoh et al., Applied and Environmental Microbiology, 71 (5): p. 2789-2792 (2005)). Yeasts naturally do not produce lactic acid and, thus, for lactic acid production by yeast, a gene coding a L-lactate dehydrogenase, an enzyme converting pyruvic acid into L-lactic acid, (hereinafter, abbreviated as L-ldh gene) should be introduced into the yeast by a gene recombination technique.

Bovine-derived L-ldh genes have been studied as the L-ldh gene for introduction to yeast (see Japanese Patent Application National Publication (Laid-Open) No. 2001-516584 and JP-A No. 2003-259878 and Danilo Porro et al., Biotechnol. Prog., 11: p. 294-298 (1955), Danilo Porro et al., Applied and Environmental Microbiology, 65(9): p. 4211-4211 (1999) and Satoshi Saitoh et al., Applied and Environmental Microbiology, 71(5): p. 2789-2792 (2005)), and are reported to be more favorable than lactic bacterium-derived L-ldh genes. The bovine-derived L-ldh genes have a lower yield to sugar of L-lactic acid and, thus, there was a need for further improvement of yield to sugar (see Satoshi Saitoh et al., Applied and Environmental Microbiology, 71(5): p. 2789-2792 (2005)). In addition, improvement of L-lactic acid productivity by mutation of the yeast-derived gene has also been studied. However, mutation of yeast-derived gene often resulted in disadvantages such as elongation of fermentation period and deterioration in sugar-consumption rate (see Japanese Patent Application National Publication (Laid-Open) No. 2001-516584 and JP-A No. 2006-006271).

As described above, L-lactic acid production by yeast is a useful method. However, there exists a need for further improvement in its productivity.

SUMMARY

We provide yeast comprising an introduced gene coding a *Homo sapiens*- or frog-derived L-lactate dehydrogenase.

The yeast preferably comprises an introduced gene coding a *Homo sapiens*- or *Xenopus laevis*-derived L-lactate dehydrogenase.

Other preferable yeasts include:

(1) yeast comprising an introduced gene coding a *Homo sapiens*- or frog-derived L-lactate dehydrogenase, having a DNA sequence in which part of the DNA sequence of the wild-type PDR13 gene is modified by deletion, insertion or substitution that allows translation of part of the protein coded on the gene;

(2) yeast comprising an introduced gene coding a *Homo sapiens*- or frog-derived L-lactate dehydrogenase that contains a variant alcohol dehydrogenase comprising an amino acid sequence in which part of the amino acid sequence of the wild-type alcohol dehydrogenase is substituted, deleted, inserted and/or added, wherein the variant alcohol dehydrogenase shows temperature sensitivity that the intercellular alcohol dehydrogenase activity disappears or reduces according to change in cultivation temperature; or (3) yeast comprising an introduced gene coding a *Homo sapiens*- or frog-derived L-lactate dehydrogenase that lacks the gene coding pyruvate decarboxylase 1 and has a variant pyruvate decarboxylase 5 gene in which part of the DNA sequence of the gene coding wild-type pyruvate decarboxylase 5 is deleted, inserted, substituted and/or added.

EXPLANATION OF NUMERALS

Figure 1:
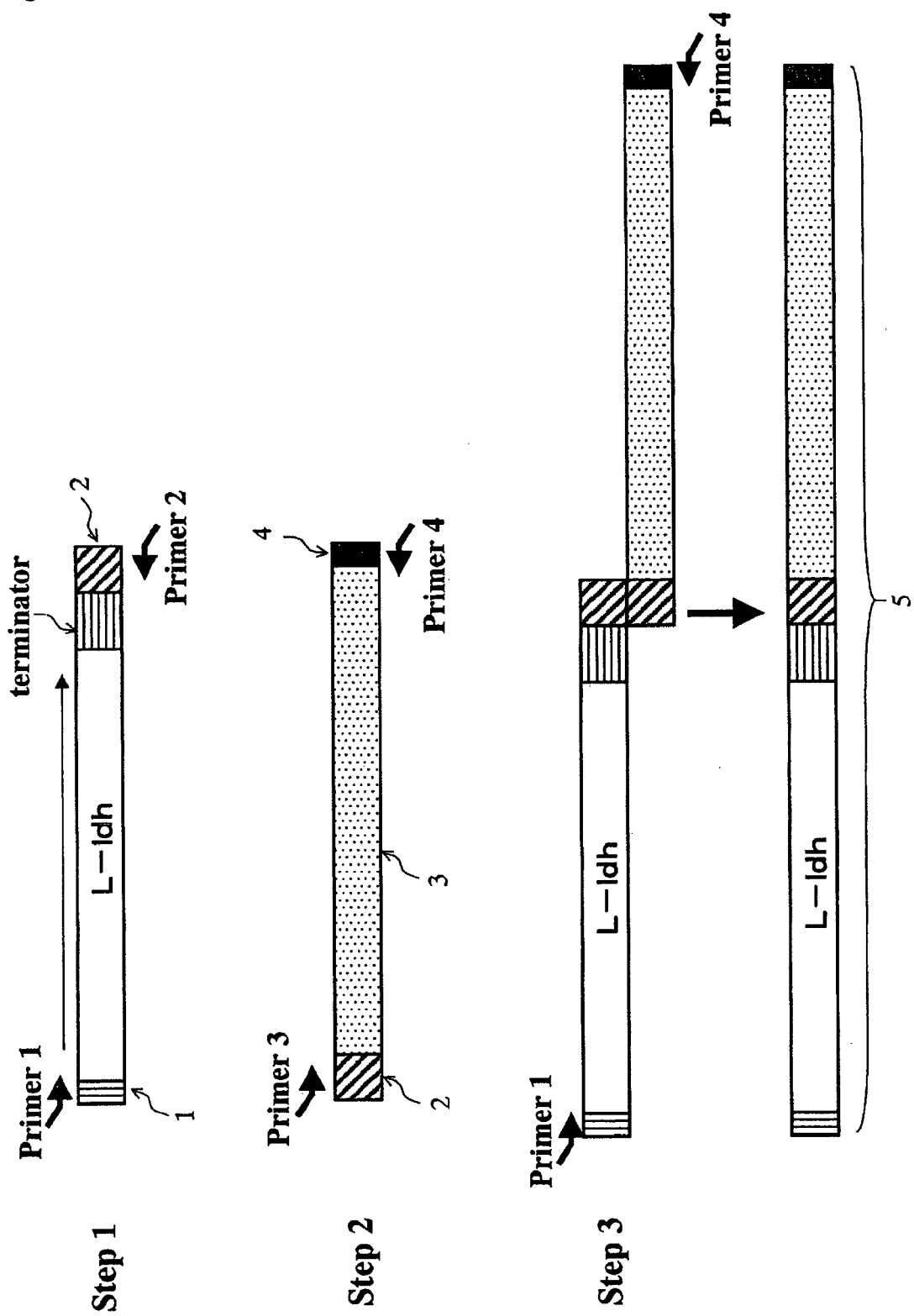
FIG. 1 is a schematic chart showing an example of the method for preparing a PCR fragment for introduction of the L-ldh gene into chromosome.

1: Homologous sequence upstream of desired introduction site (addition site)
2: Common sequence
3: Yeast selection marker gene
4: Homologous sequence upstream of desired introduction site (addition site)
5: PCR fragment for introduction of L-ldh gene into chromosome

DETAILED DESCRIPTION

An aspect of the disclosure is yeast comprising an introduced gene coding a *Homo sapiens*- or frog-derived L-lactate dehydrogenase (L-ldh gene).

The L-ldh gene represents a gene coding the protein that converts reduced nicotinamide adenine dinucleotide (NADH) and pyruvic acid into oxidized nicotinamide adenine dinucleotide (NAD+) and L-lactic acid. The gene coding a L-lactate dehydrogenase (L-ldh gene) is not particularly limited, if it is a *Homo sapiens*- or frog-derived gene. The *Homo sapiens*-derived gene is a *Homo sapiens*-derived L-ldh gene, and the frog-derived genes include L-ldh genes of the frogs belonging to Rhacophoridae, Ranidae, Hylidae, Microhylidae, Bufonidae, Hyperoliidae, Pelobtainae, Discoglossidae, and Pipidae. Among them, the frog-derived L-ldh gene is preferably a L-ldh gene derived from a frog belonging to Pipidae, and among the Pipidae frogs, a L-ldh gene derived from *Xenopus laevis* is particularly preferable.

The three kinds of isoforms of the gene coding a *Homo sapiens*- or frog-derived L-lactate dehydrogenase (L-ldh gene), ldhA, ldhB, and ldhC, are known, and any one of them may be used. The ldhA gene is preferred.

Specifically, the gene coding *Homo sapiens*-derived L-lactate dehydrogenase (L-ldh gene) is preferably the L-ldh gene having the nucleotide sequence shown in SEQ ID No. 1. Alternatively, the frog-derived the gene coding a L-lactate dehydrogenase (L-ldh gene) is preferably the L-ldh gene having the nucleotide sequence shown in SEQ ID No. 2.

The genes coding a *Homo sapiens*- or frog-derived L-lactate dehydrogenase (L-ldh gene) include genetic polymorphism an also variant gene generated by mutagenesis. The genetic polymorphism means partial change in the DNA sequence of a gene caused by natural mutation. The mutagenesis is artificial introduction of mutation into a gene. Mutagenesis is performed, for example, by a method of using a site-specific mutagenesis kit (Mutan-K, manufactured by Takara Bio Inc.) or a method of using a random mutagenesis kit (BD Diversify PCR Random Mutagenesis (manufactured by CLONTECH)). The *Homo sapiens*- or frog-derived L-ldh gene may have a DNA sequence partially deleted or inserted, if the gene codes a protein having an activity to convert NADH and pyruvic acid into NAD+ and L-lactic acid.

The yeast comprising an introduced gene coding a *Homo sapiens*- or frog-derived L-lactate dehydrogenase (L-ldh gene), in particular that comprising a variant gene, produces L-lactic acid at high yield to sugar.

The yeast comprising an introduced gene coding a *Homo sapiens*- or frog-derived L-lactate dehydrogenase (L-ldh gene) is preferably yeast comprising a DNA sequence in which part of the DNA sequence of the wild-type PDR13 gene is modified by deletion, insertion or substitution that allows translation of part of the protein coded on the gene.

The wild-type PDR13 gene is preferably a gene having the DNA sequence shown in SEQ ID No. 64. The variant PDR13 gene is preferably yeast having the gene having the DNA sequence shown in SEQ ID No. 22. In addition, part of the protein coded on the wild type or variant PDR13 gene preferably has the primary amino acid sequence shown in SEQ ID No. 23.

The yeast comprising an introduced gene coding a *Homo sapiens*- or frog-derived L-lactate dehydrogenase (L-ldh gene) is preferably yeast partially producing the PDR13 protein. Yeasts partially producing the PDR13 protein have a variant PDR13 gene, i.e., a gene coding a variant PDR13 protein. Examples of the mutations include mutation (deletion) of part of the yeast chromosomal DNA coding the PDR13 protein, mutation (deletion or substitution) of one or more amino acids in the protein amino acid sequence, and the like.

An example of the "deletion of part of the chromosomal DNA coding the PDR13 protein" is a variant DNA having a mutation prohibiting translation of at least C-terminal side 39 amino acid residues in the DNA sequence of chromosomal DNA. The mutation of at least C-terminal side 39 amino acids deleted from the amino acid sequence of the PDR13 protein is prepared by introduction mutation into the chromosomal DNA coding the PDR13 protein by site-specific mutagenesis method.

The site-specific mutagenesis may be performed, for example, by using mutagenesis method of a site-specific mutagenesis kit (Mutan-K, manufactured by Takara Bio Inc.), but the mutagenesis method is not limited to thereto.

The yeast comprising an introduced gene coding a *Homo sapiens*- or frog-derived L-lactate dehydrogenase (L-ldh gene) preferably has a variant alcohol dehydrogenase having an amino acid sequence in which part of the amino acid sequence of the wild-type alcohol dehydrogenase is substituted, deleted, inserted and/or added.

The yeast comprising an introduced gene-coding a *Homo sapiens*- or frog-derived L-lactate dehydrogenase (L-ldh gene) is preferably yeast having a temperature-sensitivity that its intercellular alcohol dehydrogenase activity of the wild-type alcohol dehydrogenase disappears or reduces by change in cultivation temperature.

The alcohol dehydrogenase is a protein that converts acetaldehyde into ethanol.

A yeast has multiple isogenes as the genes coding an alcohol dehydrogenase. It is preferable to use an alcohol dehydrogenase gene having the highest alcohol dehydrogenase activity in the yeast cells for use in production.

Specifically, known alcohol dehydrogenase isogenies of *Saccharomyces cerevisiae* registered in the *Saccharomyces* Genome Database include ADH1, ADH2, ADH3, ADH4, ADH5, ADH6, ADH7, and others. Among them, use of ADH1 gene is preferable.

The yeast comprising an introduced gene coding a *Homo sapiens*- or frog-derived L-lactate dehydrogenase (L-ldh gene) is preferably a yeast lacking the gene coding pyruvate decarboxylase 1 and having a variant pyruvate decarboxylase 5 gene having a DNA sequence in which part of the DNA sequence of the gene coding the wild-type pyruvate decarboxylase 5 is deleted, inserted, substituted and/or added.

The yeast comprising an introduced gene coding a *Homo sapiens*- or frog-derived L-lactate dehydrogenase (L-ldh gene) is preferably yeast lacking its PDC1 gene. Deletion of the PDC1 gene leads to deterioration in pyruvate decarboxylase activity, compared to the wild-type PDC1 gene. Deletion of both genes PDC1 and PDC5 is known to lead further deterioration in the pyruvate decarboxylase activity and also to extremely slow growth in a glucose-containing medium. Thus, preferably, it becomes possible to reduce the PDC5 gene-derived pyruvate decarboxylase activity favorably and to control the metabolic route of yeast to ethanol by introducing mutation in the PDC5 gene.

Specifically, the yeast is preferably a yeast having a specific activity of its intercellular pyruvate decarboxylase preferably at ⅓ or less of the specific activity in the wild-type yeast cell. Deletion of the PDC1 gene allows reduction of the specific pyruvate decarboxylase activity in yeast cell to ⅓ or less of the wild-type yeast specific activity. The specific pyruvate decarboxylase activity in yeast cell can be determined using the method described below.

The yeast is not particularly limited, if it is a yeast-allowing introduction of the *Homo sapiens*- or frog-derived L-ldh gene, and examples thereof include yeasts belonging to *Saccharomyces*, *Schizosaccharomyces* and *Kluyveromyces* species. *Saccharomyces cerevisiae* is preferred, particularly, NBRC10505 or NBRC10506.

Hereinafter, the method of producing the yeast will be described more specifically, but the yeast can be produced by a variety of methods. First, various methods of producing the yeast will be described.

A desired gene may be coned by a method of obtaining a desired gene region by the PCR (Polymerase Chain Reaction) method based on known gene information, a method of cloning from genomic and cDNA libraries using homology or enzyme activity as an indicator, and the like. Other methods include methods of preparing the clone by chemical synthesis or genetic engineering based on known protein information.

The plasmid to which the cloned desired gene is introduced may be any one of the plasmids generally used in yeast. The plasmids generally used in yeast have a sequence needed for autonomous replication in yeast cell, a sequence needed for autonomous replication in *E. coli* cell, a yeast selection marker and an *E. coli* selection marker. Alternatively, the expression plasmid for expression of the introduced desired gene preferably has so-called regulatory sequences regulating expression of the desired gene such as operator, promoter, terminator and enhancer. The sequence needed for autonomous replication in yeast cell is, for example, a set of yeast autonomous replication origin (ARS1) and centromere sequence or a yeast 2-µm plasmid replication origin, while the sequence needed for autonomous replication in *E. coli* is, for example, *E. coli* ColE1 replication origin.

The yeast selection marker is, for example, an auxotrophic complementary gene such as URA3, LEU2, TRP1 or HIS3 or a drug-resistant gene such as G418-resistant gene or neomycin-resistant gene. The *E. coli* selection marker is, for example, an antibiotic-resistant gene such as ampicillin-resistant gene or kanamycin-resistant gene.

The regulatory sequence is not particularly limited, if it is a sequence allowing expression of a desired gene, and examples thereof include promoter and terminator regions of the genes coding the proteins highly expressed in yeast such as alcohol dehydrogenase (ADH), triose phosphate dehydrogenase (TDH), pyruvate decarboxylase (PDC), and cytochrome C1 (CYC1). However, the expression plasmid is not limited thereto.

The methods of introducing a DNA such as plasmid, expression plasmid, linearized plasmid, linearized expression plasmid, or PCR fragment into yeast include transformation, transduction, transfection, cotransfection and electroporation, and the like, and specifically, for example, it can be performed by a transformation method such as a method of using lithium acetate (Journal of bacteriology, 1983, Vol. 153, pp. 163-168) or a protoplast method (Satoshi Harashima et al., Molecular Cell Biology, 1984, Vol. 4, pp. 771-778). Alternatively, it may be performed by, for example, ALKALI CATION YEAST TRANSFORMATION KIT available from BIO101. Among them, the method of using lithium acetate is preferable in the present invention, but the method is not limited thereto.

Any one of the known methods described, for example, in "Methods in Yeast Genetics, 1990, M. D. Rose et al." may be used as the method of culturing the transformed yeast obtained by the transformation method. The selection medium is arbitrary, if it is a minimum medium containing no nutrient for the marker gene used as an indicator of the introduction of plasmid, expression plasmid, or PCR fragment. Favorable is a medium having the following composition: Yeast nitrogen base without amino acids (manufactured by DIFCO) 0.67%, glucose 2.0%, dropout mixture with the nutrient for marker gene removed (a medium described in the Methods in Yeast Genetics above), but the medium is not limited thereto.

Deletion of the desired gene can be performed by homologous recombination of the desired gene locus with a selection marker such as an auxotrophic marker gene or a drug-resistant gene commonly used in yeast. Examples thereof include, but are not limited to, auxotrophic marker genes such as URA3, LEU2, TRP1, and HIS3 (Methods in Enzymology, Vol. 101, pp. 202-211, G-418) and drug-resistant genes (Gene, 1083, Vol. 26, pp. 243-253).

The method of introducing the *Homo sapiens*- or frog-derived L-ldh gene into yeast is, for example, a method of cloning the *Homo sapiens*- or frog-derived L-ldh gene and trans-forming yeast with an expression plasmid having the cloned gene incorporated, a method of inserting the cloned gene at a desired position of chromosome by homologous recombination, or the like, but is not limited thereto.

A plasmid capable of expressing the gene is obtained by introducing the *Homo sapiens*- or frog-derived L-ldh gene into the expression plasmid described above at the position downstream of the promoter. It is possible to introduce the *Homo sapiens*- or frog-derived L-ldh gene into yeast by transforming the yeast with the *Homo sapiens*- or frog-derived L-ldh gene-expressing plasmid obtained by the method described below.

The yeast is preferably yeast comprising the gene coding a L-lactate dehydrogenase introduced expressively at a position downstream of the promoter for pyruvate decarboxylase 1 gene on chromosome.

The method of inserting the *Homo sapiens*- or frog-derived L-ldh gene at a desired position on chromosome, preferably downstream of the promoter for pyruvate decarboxylase 1 gene (PDC1 gene), by homologous recombination is, for example, a method of performing PCR (Polymerase Chain Reaction) using a primer designed to add homologous regions at desired positions upstream and downstream of the *Homo sapiens*- or frog-derived L-ldh gene and transforming the obtained PCR fragments into yeast by the method described below, but is not limited thereto. The PCR fragment preferably has a yeast selection marker for easier selection of the transformed yeast.

The method of preparing the PCR fragment for use may be performed, for example, in the following three steps (1) to (3). These steps are shown in FIG. 1:

(1) Step 1: The fragment containing a *Homo sapiens*- or frog-derived L-ldh gene and a terminator downstream thereof is amplified by PCR, using a plasmid having the *Homo sapiens*- or frog-derived L-ldh gene and the terminator (used as a template) and a set of primers 1 and 2. The primer 1 is designed to add a homologous sequence of 40 bp or more to a position upstream of the desired position, while the primer 2 is designed, based on the plasmid-derived sequence downstream of the terminator. Preferably, the homologous sequence added to the primer that is homologous to the upstream of the desired position is preferably a sequence homologous to the upstream of the PDC1 gene.

(2) Step 2: A fragment containing a yeast selection marker is amplified by PCR, using a plasmid containing a yeast selection marker such as pRS424 or pRS426 as a template and a set of primers 3 and 4. The primer 3 is designed to add a sequence of 30 bp or more that is homologous to the sequence downstream of the terminator of the PCR fragment in Step 1, while the primer 4 is designed to add a sequence of 40 bp or more that is homologous to downstream of the desired position. Preferably, the sequence added to the primer 4 that is homologous to the sequence downstream of the desired position is a sequence homologous to downstream of the PDC 1 gene.

(3) Step 3: PCR of the mixture of the PCR fragments obtained in Steps 1 and 2 as templates and a set of primers 1 and 4 gave PCR fragments containing *Homo sapiens*- or frog-derived L-ldh genes containing the sequences homologous to upstream and downstream of the desired position added at both terminals, terminators and yeast selection markers. Preferably, the PCR fragments are PCR fragments containing *Homo sapiens*- or frog-derived L-ldh genes containing sequences homologous to upstream and downstream of the PDC1 gene added at both terminals, a terminator and a marker gene.

When a yeast selection marker is introduced by introducing the *Homo sapiens*- or frog-derived L-ldh gene-expressing plasmid thus obtained or the PCR fragments into yeast, it is possible to obtain the transformed yeast with the marker as indicator.

It is possible to produce L-lactic acid in the medium by culturing the yeast having an introduced *Homo sapiens*- or frog-derived L-ldh gene. If the expression plasmid introduced is retained in the yeast, it is possible to produce L-lactic acid in the medium by culture of the transformed yeast. The L-lactate dehydrogenase activity is an activity of converting pyruvic acid and NADH into L-lactic acid and NAD+. The L-lactate dehydrogenase activities are often compared in their specific activities as an indicator. Specifically, yeasts of the same L-ldh gene-introducing method and genetic background are cultured under the same condition, and the change absorbance at 340 nm associated with decrease of NADH is determined using the protein extracted from the culture microorganism. When an enzyme amount of reducing 1 µmol of NADH per minute at room temperature is defined as 1 unit, the specific activity of L-lactate dehydrogenase is expressed by the Formula 1, wherein, Δ340 represents the decrement in absorbance at 340 nm per minute, and 6.22 is the millimolar absorption coefficient of NADH.

$$LDH \text{ specific activity (Unit/mg)} = \frac{\Delta 340 \times \text{Total volume of reaction solution (ml)}}{\left[\frac{\text{Enzyme solution concentration (mg/ml)} \times}{\text{Enzyme solution volume (mL)}}\right] \times 6.22 \times \text{Optical path length (cm)}}$$ Formula 1

Hereinafter, a method of preparing yeast containing a partially variant PDR13 protein-coding gene will be described. Examples of the preparation methods include:

(1) A method of selecting a yeast having a lactic acid-production efficiency higher than that of the parent strain from a recombinant yeast library prepared by insertion of a transposon into the yeast chromosomal DNA;
(2) A method of preparing a yeast containing a partially deficient gene coding the PDR13 protein, for example, by a homologous recombination method; and
(3) A method of preparing a microorganism having, on the chromosome, a DNA coding a variant amino acid sequence having a mutation such as deletion, substitution or insertion, prohibiting translation of at least C-terminal side 39 amino acid residues in the amino acid sequence of the PDR13 protein, for example, by a homologous recombination method or others.

The parent strain described in method (1) is a parent strain supplied to the mutagenesis processing, and the parent strain may be wild-type yeast, an industrially useful modified variant yeast, cell-fusion yeast or a recombination yeast prepared by a genetic engineering method.

The gene mutation library described in (1) is prepared, for example, by a method of preparing transposon sequence-inserted DNA fragments by restriction enzyme digestion of the transposon sequence-inserted genome library provided as Yeast mTn Plasmid Collection (manufactured by Open Biosystems) and introducing the DNA fragments into the chromosomal DNA in two homologous recombination process.

It is possible to observe the influence of insertion mutation in a definitely limited gene region on the lactic acid-production efficiency, by identifying the transposon sequence insertion site using the gene mutation library as a screening source.

The method of selecting a yeast having an improved lactic acid-production efficiency from the library is, for example, a method of introducing an expression plasmid of the gene coding lactic acid-producing enzyme to each strain in the library, culturing the obtained transformant yeast, and measuring the lactic acid generated quantitatively. Increase in accumulated lactic acid over cultivation period indicates greater production of lactic acid.

The selection of yeast higher in lactic acid-production efficiency from the library can be preformed by using a L-ldh gene-introduced yeast as the parent strain. The kind of the introduced L-ldh used is not particularly limited, but it is preferably a *Homo sapiens*-, frog- or bovine-derived L-ldh gene having the nucleotide sequence shown in SEQ ID No. 1, 2 or 3.

Figure 2:
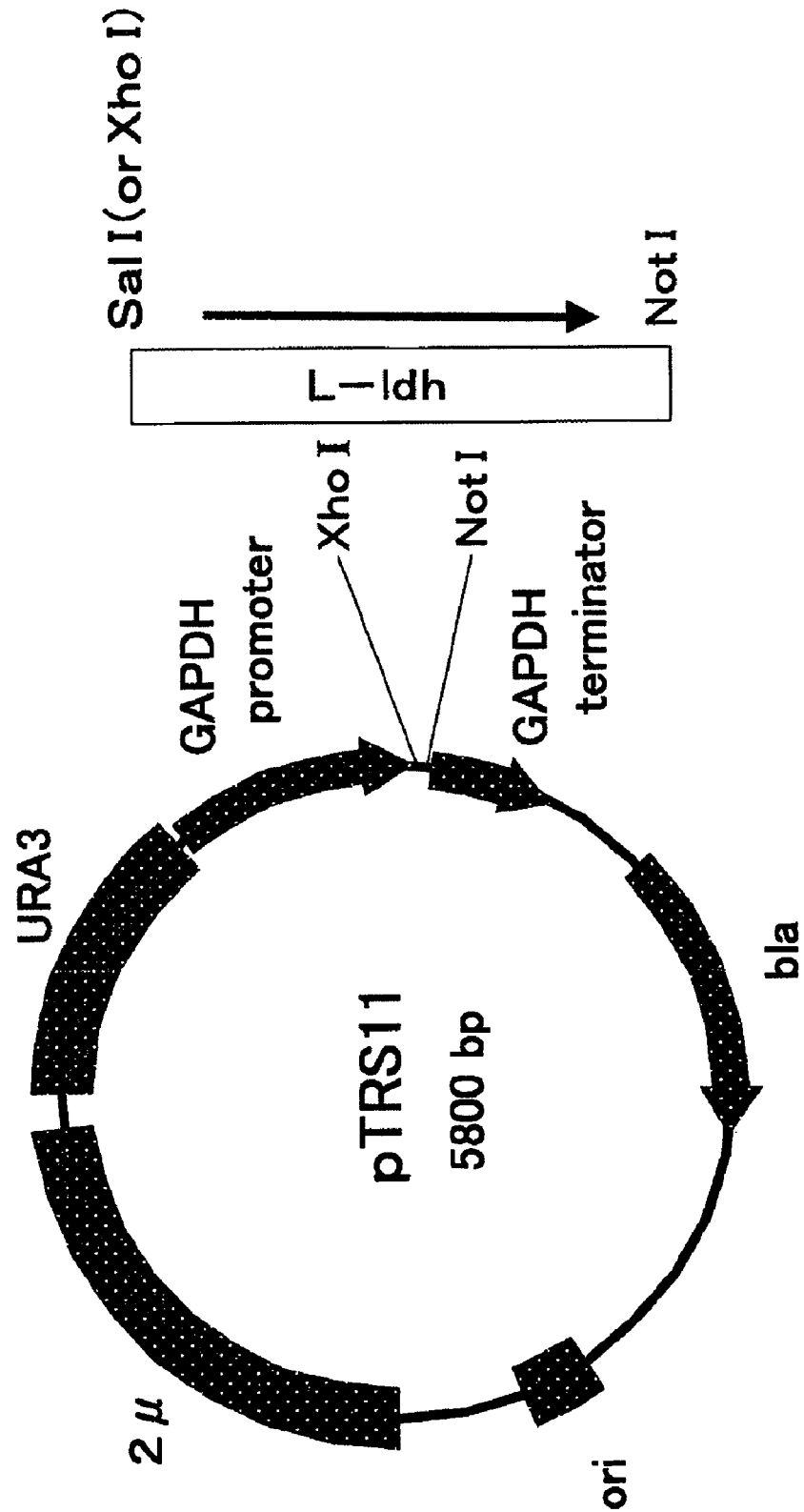
FIG. 2 is a chart showing plasmid pTRS11, an example of an expression plasmid.
Figure 3:
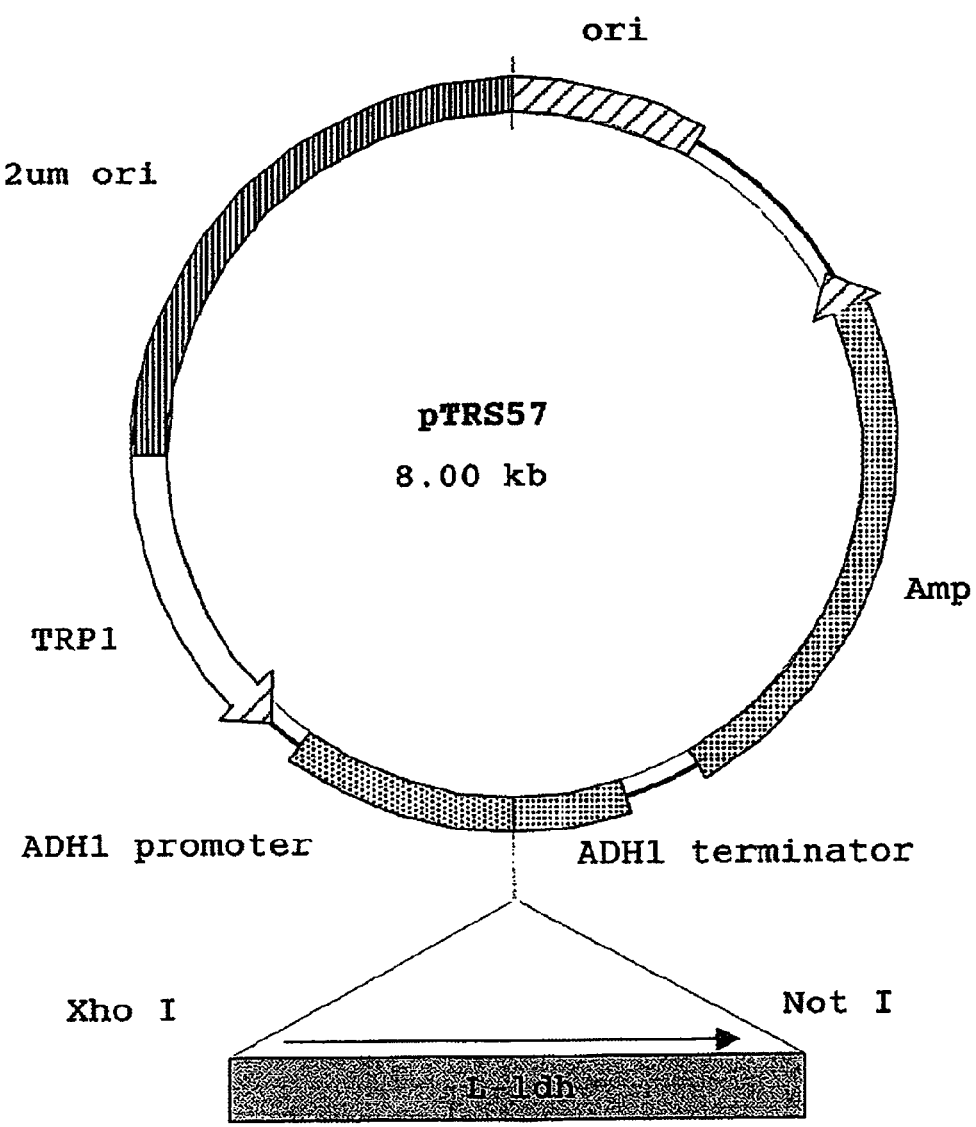
FIG. 3 is a chart showing plasmid pTRS57, an example of an expression plasmid.

FIG. 3 is a chart showing the structure of a bovine-derived L-Ldh-expressing plasmid pTRS57, while FIG. 2 is a chart showing the structure of a plasmid pTRS11.

The expression form of the L-ldh gene, for example whether it is expressed as it is introduced into chromosome or plasmid, is not particularly limited, if the gene is connected under the control of a promoter allowing expression of the gene. Examples of the expression plasmids include a multi-copy expression plasmid pTRS57 prepared by binding a gene structure containing a bovine-derived L-Ldh gene under the control of alcohol dehydrogenase 1 gene promoter bound to pRS426, and a multicopy expression plasmid pTRS48 prepared by inserting a *Homo sapiens*-derived L-Ldh gene to pTRS11.

It is possible to select a yeast having a lactic acid-production efficiency improved from the parent strain, by preparing transformed yeasts by introducing pTRS57 into the strains in the library by a ordinary method, culturing the transformed yeasts and the parent strain used for transformation respectively, and determining the amount of the lactic acid produced during culture.

The culture method of the transformed yeasts containing pTRS57 is not particularly limited, if it is a culture allowing expression of L-lactate dehydrogenase, and may be performed by a culture method of transformed yeast.

The concentration of lactic acid in the culture solution can be determined quantitatively by a method of using HPLC. For example, the culture solution supernatant is separated by centrifugation of the culture solution; the concentration of lactic acid in the culture solution is determined using the supernatant as an analytical sample and measuring the electrical conductivity of the eluent from an anion exchange column for lactic acid assay.

It is possible to obtain yeasts having lactic acid-production efficiency higher than that of the parent strain, by selecting yeast showing lactic acid productivity higher than the parent strain after culture for the same period.

An example of the yeast obtained by the method, higher in lactic acid-production efficiency is, for example, *Saccharomyces cerevisiae* having a transposon DNA fragment inserted into the gene coding the PDR13 protein (hereinafter, referred to simply as PDR13 gene) on the chromosomal DNA.

(2) The method of producing yeast containing a partially deficient gene coding the PDR13 protein by a homologous recombination method is, for example, a method of using yeast allowing homologous recombination on chromosome DNA with a straight-chain DNA. An example of the straight-chain DNA is a straight-chain DNA arranged with DNAs homologous to the sequence in or close to the PDR13 gene at both terminals of the TRP1 gene.

It is possible to prepare a partially PDR13 gene-deficient yeast by introducing the straight-chain DNA into a yeast allowing homologous recombination of chromosome with a straight-chain DNA by ordinary method and selecting a tryptophan requiring strain.

(3) The method of preparing a microorganism having a DNA coding the amino acid sequence having mutation, such as deletion, substitution or insertion, prohibiting translation of at least C-terminal side 39 amino acid residues in the amino acid sequence of the PDR13 protein on the chromosome for example by a homologous recombination method is, for example, a method of preparing a variant gene coding the amino acid sequence having mutation, such as deletion, substitution or insertion, prohibiting translation of at least C-terminal side 39 amino acid residues in the amino acid sequence coded on the gene by introducing site-specific mutation in the PDR13 gene and preparing a yeast having a chromosomal DNA with its PDR13 gene substituted with a variant PDR13 gene by a homologous recombination method.

By at least the methods disclosed in (1), (2) or (3), it is possible to prepare a yeast containing an introduced gene coding a *Homo sapiens*- or frog-derived L-lactate dehydrogenase that contains a variant PDR13 gene in which part of the wild-type PDR13 gene is modified by deletion, insertion or substitution that allows translation of part of the protein coded on the gene.

The yeast, preferably a yeast comprising a variant alcohol dehydrogenase having an amino acid sequence in which part of the amino acid sequence of the wild-type alcohol dehydrogenase is modified by substitution, deletion, insertion and/or addition, wherein the variant alcohol dehydrogenase shows temperature sensitivity that the intercellular alcohol dehydrogenase activity disappears or reduces according to change in cultivation temperature.

More preferably, the yeast has a variant alcohol dehydrogenase having an amino acid sequence in which one or more amino acids in part of the amino acid sequence of the wild-type alcohol dehydrogenase are modified by substitution, deletion, insertion and/or addition. The mutation by substitution, deletion, insertion, or addition may be a single mutation or a combination of multiple mutations.

The variant alcohol dehydrogenase is preferably a variant of the wild-type alcohol dehydrogenase coded on the ADH1 gene, more preferably, a variant of the wild-type alcohol dehydrogenase 1 comprising the primary amino acid sequence shown in SEQ ID No. 39. The variant alcohol dehydrogenase is more preferably a variant alcohol dehydrogenase comprising an amino acid sequence in which one or more amino acids in the amino acid sequence of the wild-type alcohol dehydrogenase 1 shown in SEQ ID No. 39 are modified by substitution, deletion, insertion and/or addition.

The variant alcohol dehydrogenase favorable for the yeast is a variant alcohol dehydrogenase consisting of an amino acid sequences shown in SEQ ID Nos. 40, 41 or 42.

The temperature-sensitivity of the variant alcohol dehydrogenase favorable for the yeast is such that the yeast containing the variant alcohol dehydrogenase, when compared with a yeast containing the wild-type alcohol dehydrogenase, has a similar alcohol dehydrogenase activity at a cultivation temperature, but loses or has a reduced alcohol dehydrogenase activity at a particular cultivation temperature or more, as the cultivation temperature is changed. Decreased activity of alcohol dehydrogenase in yeast cell results in deterioration in sugar-consumption efficiency and drastic delay in growth in sugar-containing media, and thus, it is possible to determine the presence of the sensitivity by observing the growth rate in sugar-containing media. The yeast, preferably the variant alcohol dehydrogenase, shows temperature sensitive at a cultivation temperature of 30° C. or higher, more preferably, 32° C. or higher, and still more preferably 34° C. or higher.

Hereinafter, a method of producing a yeast containing the temperature-sensitive variant alcohol dehydrogenase will be described, by taking a yeast having a temperature-sensitive variant ADH1 gene as an example, but it does not mean that the variant gene is limited to the ADH1 gene and thus, the method of producing the yeast is also not limited to the following method.

First, yeast lacking the wild-type ADH1 gene is prepared. Deletion may be performed by the deletion method of a desired gene described above. Deletion of the ADH1 gene, which is most responsible for the alcohol activity in yeast cell, results in deterioration in sugar (including glucose)-consumption efficiency and drastic decrease in growth rate in sugar-containing media. It is possible to screen the temperature-sensitive variant ADH1 gene from the randomly mutated ADH1 genes by using the properties described above. When transformed yeasts having random variant ADH1 genes introduced are cultured in a glucose-containing medium at normal cultivation temperature (room temperature to 30° C.), yeasts having an ADH1 gene inactivated by mutagenesis do not grow, and thus, it is possible to select only yeasts carrying the ADH1 gene, which retain their activity at the temperature, by observing growth. Then, when selected yeasts are cultured in a glucose-containing medium at a temperature other than normal cultivation temperature (30° C. or higher, or room temperature or lower), yeasts carrying the temperature-sensitive variant ADH1 gene do not grow, and thus, it is possible to perform negative screening of the yeasts having a temperature-sensitive variant ADH1 gene introduced. Specifically, for example it is possible to prepare yeast showing the sensitivity at each temperature by observing growth of transformed yeasts growing by culture at 25° C. in a glucose-containing medium at 30° C., 34° C. and 37° C., but the cultivation temperature is not limited thereto.

The methods of preparing a temperature-sensitive variant yeast include screening in nature, mutational methods such as chemical treatment, for example with nitroso-guanidine or ethyl methanesulfonate and UV irradiation, and genetic engineering, for example by PCR reaction.

Methods of introducing mutation at a particular gene by genetic engineering include random mutagenesis methods and site-specific mutagenesis methods. In the case of the former random mutagenesis method, a variant gene is prepared, for example, using a random mutagenesis kit (BD Diversify PCR Random Mutagenesis (manufactured by CLONTECH)), and in the case of the site-specific mutagenesis method, it is prepared for example, using a site-specific mutagenesis kit (Mutan-K (Takara Bio Inc.)). Among the methods above, a preparation method of genetic engineering is preferable, but the preparation method is not limited thereto.

The variant ADH1 gene thus obtained is introduced by a gap reparation method ("Experiments in Yeast Molecular Genetics," Japan Scientific Societies Press, 1996), the subject matter of which is incorporated by reference. When autonomously replicating plasmids containing the variant ADH1 gene DNA fragments and the ADH1 gene cloned that has deletion in the ADH1 gene and is linearized are introduced into yeast cell simultaneously, homologous recombination of the variant ADH1 gene DNA fragments with the homology sequences at both terminals of the deleted region follows, causing reparation of the deleted region and simultaneously restoration of the autonomously replicating capacity by ring-closure of the plasmids. More specifically, it is possible to obtain a cyclic plasmid containing a cloned variant ADH1 gene having random mutation in the targeted mutagenesis region, by introducing a plasmid without a targeted mutagenesis region DNA obtained by cleavage of a ADH1 gene-cloned plasmid with a suitable restriction enzyme and fragments amplified with a suitable primer while introducing random mutagenesis in the ADH1 gene region, simultaneously into a ADH1-deleted yeast.

The plasmid for the mutagenesis by the gap reparation method may be any one of the plasmids generally used in yeast. Preferably, for example, a plasmid such as YCp50, pRS315, pRS316, pAUR112 or pAUR123, which has a limited copy number in yeast cell, may be used, but the plasmid is not limited thereto. The ADH1 gene region introduced then preferably include additionally so-called regulatory sequences regulating expression of the gene present upstream and downstream of the gene such as operator, promoter, terminator and enhancer. It is thus possible to prepare a temperature-sensitive variant ADH1 gene cloned in plasmid.

Hereinafter, a method of preparing yeast having a temperature-sensitive variant ADH1 gene will be described.

The plasmid having the cloned temperature-sensitive variant ADH1 gene is obtained from the transformed yeast. The preparation method is not particularly limited, and, for example, a commercially available yeast plasmid recovery kit, such as YEASTMAKER Yeast Plasmid Isolation Kit (Clontech), may be used. Transformation of the adh1-deleted yeast prepared above with the plasmid obtained that is digested with a restriction enzyme that does not cleave the ADH1 gene sequence and subsequent linearized results in recombination of the DNA sequence close to the ADH1 gene locus and the homologous region in the linearized plasmid DNA sequence and substitution of the marker gene used during deletion of ADH1 with the temperature-sensitive variant ADH1 gene, finally giving a desirable yeast having a temperature-sensitive variant ADH1 gene. The processing may be performed according to the "pop-in/pop-out method" (described in Methods in Enzymology, 1987, Vol. 154, pp. 164-174), the subject matter of which is incorporated by reference.

The method of confirming the temperature sensitivity of alcohol dehydrogenase is, for example, a method of observing the oxidation reaction of alcohol dehydrogenase from ethanol to acetaldehyde with a homogenate of the yeast cell cultured at a sensitive temperature and confirming the temperature sensitivity using the fact that the activity of the homogenate of variant gene-containing yeast cells is lower in sensitivity than that of the wild-type gene-containing yeast cell as an indicator.

The alcohol dehydrogenase activity can be determined, by considering the measurement condition such as temperature and pH by taking into consideration the environment of each alcohol dehydrogenase isozyme catalyzing the reaction and measuring the substrate affinity to ethanol under the condition. For example, the enzyme activity of the alcohol dehydrogenase coded by *Saccharomyces cerevisiae* ADH1 gene at a cultivation temperature of 34° C. is determined using the homogenate of the culture cultured and harvested at a cultivation temperature of 34° C. and the substrate ethanol under an environment at a pH adjusted to 8.8 with a tris-hydrochloric acid buffer solution and a reaction temperature of 30° C. The activity can be evaluated by observing the absorbance change at a wavelength of 340 nm associated with the reductive reaction from oxidized nicotinamide dinucleotide (NAD+) to reduced nicotinamide dinucleotide (NADH), which occurs simultaneously with the oxidation reaction from ethanol to acetaldehyde. If the enzyme amount decreasing 1 µmol of NADH per minute at room temperature is defined as a unit, the specific activity of alcohol dehydrogenase is shown by Formula (2), wherein, $\Delta 340$ nm represents the decrement in absorbance at 340 nm per minute, and 6.22 is the millimolar absorption coefficient of NADH.

$$\text{Specific activity of alcohol dehydrogenase (mmol/min/µg)} = \frac{\Delta 340 \times \text{reaction solution amount } (\mu l) \times 10^{-6}}{\substack{\text{Homogenate protein concentration } (\mu g/\mu l) \times \\ \text{Homogenate amount } (\mu l) \times 6.22 \times \\ \text{Optical path length (cm)}}} \quad \text{Formula 2}$$

It is possible to evaluate the temperature sensitivity of the variant alcohol dehydrogenase under the cultivation temperature, by measuring the alcohol dehydrogenase activity of the homogenate of the variant yeast cell and the wild-type yeast cell cultured at each cultivation temperature under the same condition and comparing the calculated specific activities of alcohol dehydrogenase.

It is possible, by the methods disclosed above, to prepare a yeast having an introduced gene coding a *Homo sapiens*- or frog-derived L-lactate dehydrogenase (L-ldh gene) that has a variant alcohol dehydrogenase consisting of an amino acid sequence in which part of the amino acid sequence of the wild-type alcohol dehydrogenase is modified by substitution, deletion, insertion and/or addition, wherein the variant alcohol dehydrogenase shows temperature sensitivity that the intercellular alcohol dehydrogenase activity disappears or reduces according to change in cultivation temperature.

There are three kinds of genes coding the yeast pyruvate decarboxylasse (PDCs); pyruvate decarboxylase 1-coding gene (PDC1 gene), pyruvate decarboxylase 5-coding gene (PDC5 gene) and pyruvate decarboxylase 6-coding gene (PDC6 gene). Among them, the genes having a major function as pyruvate decarboxylase are PDC1 and PDC5 genes.

The yeast preferably lacks the PDC1 gene deleted, but has a variant PDC5 gene having a DNA sequence in which part of the DNA sequence of the wild-type PDC5 gene is deleted, inserted, substituted and/or added. The mutation by deletion, insertion, substitution and/or addition of partial nucleotides may be a single mutation or a combination of multiple mutations.

More preferably, the yeast is a gene in which the DNA sequence of the wild-type pyruvate decarboxylase 5-coding gene is the gene having the DNA sequence shown in SEQ ID No. 51.

The variant PDC5 gene contained in the yeast is preferably a mutant of the wild-type PDC5 gene having the DNA sequence shown in SEQ ID No. 51. More preferably, the yeast is a gene having the DNA sequence wherein the variant pyruvate decarboxylase 5-coding gene is the gene shown in SEQ ID No. 52 or 53.

The variant pyruvate decarboxylase 5 contained in the yeast is preferably temperature-sensitive. When the pyruvate decarboxylase 5 is temperature-sensitive, the yeast having the variant pyruvate decarboxylase 5 has a pyruvate decarboxylase activity similar to that of the yeast having the wild-type pyruvate decarboxylase 5 at a certain cultivation temperature, but loses or has a reduced pyruvate decarboxylase activity 5 at a particular cultivation temperature or more, as the cultivation temperature is changed. Because reduction of pyruvate decarboxylase activity in yeast cell results in reduction of sugar-consumption efficiency and drastic decrease in growth rate in sugar-containing media, it is possible to determine the presence or absence of sensitivity by observing the growth rate in sugar-containing media. The variant pyruvate decarboxylase 5 is preferably a yeast temperature-sensitive at 34° C. or higher.

Mutagenesis of the PDC5 gene is performed by modification of the DNA sequence of the PDC5 gene with a normally practiced method. Similarly to the method of modifying the ADH1 gene, it is also possible to obtain yeast having a reduced PDC5 enzyme activity by the method of preparing temperature-sensitive variants from the strains containing the PDC5 gene or the variant genes thereof. Yeasts having no detectable pyruvate decarboxylase activity grow very slowly, when cultured in a medium containing glucose as a sole carbon source. When a yeast having a reduced pyruvate decarboxylase activity is prepared using the property above, it show a growth rate similar to that of the wild-type yeast under permissive temperature condition, because the pyruvate decarboxylase activity is preserved. It is possible to obtain a desired temperature-sensitive variant PDC5 gene by preparing a variant having a growth rate drastically decreased under non-permissive temperature condition because of reduced enzyme activity.

Hereinafter, a method of preparing the yeast comprising an introduced gene coding a Homo sapiens- or frog-derived L-lactate dehydrogenase (L-ldh gene) that lacks its PDC1 gene and has a variant PDC5 gene will be described more specifically. First, for screening of the variant PDC5 gene, Δpdc1Δpdc5 double deletion yeast lacking both PDC1 and PDC5 genes is prepared. The symbol "Δ" means "deletion."

The method of preparing the Δpdc1Δpdc5 double deletion yeast may be carried out by a method of deleting a desired gene described above, but is not limited thereto. When the yeast used is a yeast belonging to *saccharomyces* species, a Δpdc1 single deletion strain and a Δpdc5 single deletion strain may be prepared by using the method of deleting a desired gene above and then, the Δpdc1Δpdc5 double deletion yeast may also be prepared from the diploids by tetrad dissection method.

Hereinafter, a method of preparing the variant PDC5 gene will be described. The preparation method may be carried out by the method of preparing the temperature-sensitive variant above. A preparation method by genetic engineering using PCR reaction will be disclosed below, but the preparation method is not limited thereto. The variant PDC5 gene can be obtained by a method of using a random mutagenesis kit BD Diversify PCR Random Mutagenesis Kit (manufactured by CLONTECH).

The variant PDC5 gene thus obtained can be introduced similarly by the gap reparation method (Experiments in Yeast Molecular Genetics, Japan Scientific Societies Press, 1996), the subject matter of which is incorporated by reference. Specifically, a cyclic plasmid containing the variant PDC5 gene having random mutation introduced in the targeted mutagenesis region is obtained, by introducing variant PDC5 gene DNA fragments and autonomously replicating plasmids containing the cloned PDC5 gene that lack the PDC5 gene and are linearized simultaneously into the Δpdc1Δpdc5 double deletion yeast.

Hereinafter, a method of preparing a Δpdc1 modified pdc5 yeast (having a variant PCD5 gene and lacking the PDC1 gene) will be described. The plasmid having a cloned variant PDC5 gene thus obtained is harvested from a transformed yeast. The preparation method is not particularly limited, and a commercially available yeast plasmid recovery kit, for example YEASTMAKER Yeast Plasmid Isolation Kit (Clontech) may be used. Subsequently, it is possible to obtain the desirable Δpdc1 modified pdc5 yeast, by transforming the Δpdc1Δpdc5 double deletion yeast thus prepared with the plasmid above digested with a restriction enzyme not cleaving the PDC5 gene sequence and linearized by using the "pop-in/pop-out method."

Hereinafter, a method of selecting yeast having an intercellular pyruvate decarboxylase activity changed by introduction of the variant PDC5 gene will be described.

The change in pyruvate decarboxylase activity can be confirmed by measuring the specific pyruvate decarboxylase activity of the homogenate of the culture of each transformant cell obtained by the gap reparation method and comparing the specific activity with that of the yeast having the wild-type PDC5 gene.

Transformed yeast cells having a variant PDC5 gene that have a specific pyruvate decarboxylase activity lower than that of the yeast having the wild-type PDC5 gene are selected by measuring the specific pyruvate decarboxylase activity of the yeasts having the variant PDC5 gene and selecting the cells having a specific enzyme activity lower than that of the yeast having the wild-type PDC5 gene. It is also possible to select more favorable yeasts by selecting trans-formed yeasts having a variant PDC5 gene showing temperature sensitivity.

Hereinafter, the method of preparing a Δpdc1 modified pdc5 yeast having a variant PCD5 gene and lacking the PDC1 gene will be described.

Plasmids having the cloned variant PDC5 gene thus obtained are collected from the transformed yeast. The preparation method is not particularly limited, and a commercially available yeast plasmid recovery kit, for example YEASTMAKER Yeast Plasmid Isolation Kit (Clontech) may be used. Transformation of the Δpdc1Δpdc5 double deletion yeast prepared above with the obtained plasmid that is previously digested with a restriction enzyme not cleaving the PDC5 gene sequence and linearized results in recombination of the DNA sequence close to the PDC5 gene locus with homologous region in the DNA sequence of the linearized plasmid with substitution of the marker gene used for deletion of the PDC5 with the variant PDC5 gene, giving a desired Δpdc1 modified pdc5 yeast. The processing may also be performed by the "pop-in/pop-out method" (described in Methods in Enzymology, 1987, Vol. 154, pp. 164-174), the subject matter of which is incorporated by reference.

A method of evaluating the intercellular pyruvate decarboxylase activity in the yeast thus selected will be described. The enzyme activity can be determined according to the method by Pronk et al. (Yeast, 1996, Vol. 12, pp. 1607-1633), the subject matter of which is incorporated by reference, which is shown briefly below as (1) to (3), with some modification as needed:

(1): Acetaldehyde is generated from the substrate pyruvic acid by pyruvate decarboxylase.
(2): Acetaldehyde generated in (1) is reduced to ethanol by alcohol dehydrogenase, by using reduced nicotinamide dinucleotide (NADH) as coenzyme.
(3): Decrease in the NADH quantity during conversion of acetaldehyde to ethanol by alcohol dehydrogenase in (2) is measured.

If the decrease in acetaldehyde amount in (2) is equivalent to the acetaldehyde amount generated in (1), the decrease in NADH amount measured in (3) is equivalent to the decrease in pyruvic acid amount in (1). Thus, the pyruvate decarboxylase activity in yeast cell can be determined by measuring the decrease in NADH amount in the reaction system.

The pyruvate decarboxylase activity in yeast cell can be compared by using its specific activity as an indicator. Specifically, proteins are extracted from yeasts cultured under the same condition, and the change in absorbance at a wavelength of 340 nm associated with decrease of NADH is determined by using each extract. When the enzyme amount decreasing 1 µmol of NADH per minute at 30° C. is defined as 1 unit, the specific pyruvate decarboxylase activity can be expressed by the following Formula 3, wherein, Δ340 represents the decrement in absorbance at 340 nm per minute, and 6.22 is the millimolar absorption coefficient of NADH. The enzyme activity can be compared by measuring the absorbance under the same condition and calculating the specific pyruvate decarboxylase activity.

$$PDC \text{ specific activity (Unit/mg)} = \frac{\Delta 340 \times \text{Total volume of reaction solution (ml)}}{\text{Enzyme solution concentration (mg/ml)} \times \text{Enzyme solution volume (mL)} 6.22 \times \text{Optical path length (cm)}} \quad \text{Formula 3}$$

It is possible, by using the method disclosed above, to prepare a yeast containing an introduced *Homo sapiens*- or *Xenopus laevis*-derived gene coding a L-lactate dehydrogenase that has a DNA sequence in which the gene coding pyruvate decarboxylase 1 is deleted and part of the DNA sequence of the gene coding wild-type pyruvate decarboxylase 5 is deleted, inserted, substituted and/or added variant pyruvate decarboxylase 5 gene.

We provide yeasts comprising a gene coding a *Homo sapiens*- or frog-derived L-lactate dehydrogenase introduced, and examples thereof include yeasts having at least two or more of the following characteristics (1) to (3):

(1) A yeast containing an introduced gene coding a *Homo sapiens*- or frog-derived L-lactate dehydrogenase that has a variant PDR13 gene, in which part of the DNA sequence of wild-type PDR13 gene is modified by deletion, insertion or substitution that allows translation of part of the protein coded by the gene, (2) A yeast containing an introduced gene coding a *Homo sapiens*- or frog-derived L-lactate dehydrogenase that has a variant alcohol dehydrogenase consisting of an amino acid sequence in which part of the amino acid sequence of the wild-type alcohol dehydrogenase is substituted, deleted, inserted and/or added, wherein the variant alcohol dehydrogenase shows temperature sensitivity that the intercellular alcohol dehydrogenase activity disappears or reduces according to the change in cultivation temperature, and (3) A yeast having an introduced gene coding a *Homo sapiens*- or frog-derived L-lactate dehydrogenase, that lacks the gene coding pyruvate decarboxylase 1 and has a variant pyruvate decarboxylase 5 gene in which part of the DNA sequence of the gene coding wild-type pyruvate decarboxylase 5 includes a deleted, inserted, substituted and/or added DNA sequence.

A method of preparing yeast containing at least two variant genes having a characteristic (1) to (3) will be described.

Specifically, such a complex yeast can be prepared by a method of using a yeast having one variant gene as the parent strain and adding another variant gene thereto. More specifically, for example in preparing a yeast having both the variant PDR13 gene and the variant ADH1 gene, it is possible to prepare a yeast having the variant PDR13 gene and the variant ADH1 gene, by preparing a yeast additionally having a variant ADH1 gene by using a yeast having a variant PDR13 gene as the parent strain. Yeasts containing other combination of variant genes can be prepared in a similar manner.

When the yeast used is a yeast belonging to *saccharomyces* species, it can be prepared from diploids of the yeasts having each variant gene by the tetrad dissection method. Specifically, for example in preparation of the yeast having both the variant PDR13 gene and the variant ADH1 gene, a yeast having the variant PDR13 gene and the variant ADH1 gene simultaneously can be prepared from a diploid in combination of a yeast having the variant PDR13 gene and a yeast having the variant ADH1 gene by the tetrad dissection method. Yeasts with other combination of variant genes can also be prepared similarly.

We additionally provide an efficient L-lactic acid-producing method. The method of producing L-lactic acid preferably contains a culture of the yeast comprising an introduced gene coding a *Homo sapiens*- or frog-derived L-lactate dehydrogenase (L-ldh gene).

In the method of producing L-lactic acid by culture of the yeast, the medium for culture of the yeast may be either a natural medium or a synthetic medium, if it is a medium containing carbon and nitrogen sources and inorganic salts for the yeast that enables efficient cultivation of the yeast.

The carbon source is not particularly limited, if it is consumed by the yeast, and examples thereof include sugars such as glucose, fructose and sucrose; syrups containing these sugars, and carbohydrates such as starch and starch hydrolysates. The carbon source may be added at once when the culture is started, as divided into portions, or continuously during culture, and used at a concentration of 10 g/l to 200 g/l.

Examples of the nitrogen sources for use include ammonia, inorganic and organic ammonium salts such as ammonium chloride, ammonium sulfate, and ammonium acetate; peptone, meat extract, yeast extract, corn steep liquor, casein hydrolysate, soy bean curd, soy bean curd hydrolysate, various fermented microorganism digestion, and the like.

Examples of the inorganic salts include magnesium phosphate, magnesium sulfate, sodium chloride, monopotassium phosphate dipotassium phosphate, ferrous sulfate, manganese sulfate, copper sulfate, calcium carbonate, and the like.

The culture may be performed, for example, by shaking culture or agitation culture. The oxygen supply condition is not particularly limited, but the culture may be carried out under aerobic condition or under micro aerobic condition. The cultivation temperature is preferably 25 to 35° C., and the culture period is normally 24 hours to 5 days. The pH of the culture solution during culture is preferably adjusted to 2.5 to 5.0, and the pH adjustment may be performed by using an alkaline solution, ammonia, calcium carbonate, or the like.

In production of L-lactic acid, the yeast is first precultured; L-lactic acid is produced in the culture solution, as the pre-culture solution is transferred into a new medium and the mixture is cultured. The cultivation temperature is not particularly limited, if proliferation of the strain is not substantially inhibited and the temperature is in the range allowing production of lactic acid, but preferably, in the temperature range of 20 to 40° C., more preferably in the range of 25 to 37° C., and still more preferably 30 to 34° C. The culture may be conducted by any method, for example, by still standing, agitation or shaking.

Culture under such a condition produces lactic acid in the medium in an amount of 1 to 20%. The method of measuring the concentration of L-lactic acid obtained is not particularly limited, but, for example, a method of using HPLC or a method of using F-kit (manufactured by Roche).

The lactic acid obtained in the culture solution can be purified by a known method. Examples thereof include a method of extracting the fermentation solution at pH 1 or lower after removal of the microorganism by centrifugation, for example with diethylether or ethyl acetate, a method of adsorbing and cleaning it on and eluting it from an ion-exchange resin, a method of distilling its ester after reaction with an alcohol under the presence of an acid catalyst, a method of crystallizing it as a calcium or lithium salt, and the like.

It is possible to produce L-lactic acid by culture of the yeast comprising an introduced gene coding a *Homo sapiens*- or frog-derived L-lactate dehydrogenase at a yield to sugar higher than that by culture of a yeast having an introduced conventional bovine-derived the gene coding a L-lactate dehydrogenase. In addition, it is also possible to improve the yield further by mutagenesis of the yeast containing an introduced gene coding a *Homo sapiens*- or frog-derived L-lactate dehydrogenase and culture of the variant strain.

EXAMPLES

Hereinafter, favorable aspects of the disclosure will be described with reference to Examples, but it should be understood that the followings are only examples and do not restrict the scope of this disclosure.

The methods in molecular genetics used in the following examples were carried out according to the methods described in "Molecular Cloning, 3rd Ed.," 1991, (U.S.), "Methods in Enzymology," 1991, (U.S.), No. 194, and "Method in Yeast Genetics, 2000 Ed.," 2000, (U.S.), the subject matter of which is incorporated by reference, unless specified otherwise.

Alternatively, the PCR method was preformed with KOD-Plus polymerase (manufactured by Toyobo) or LA-Taq (manufactured by Takara Shuzo) according to the procedure attached to the reagent, unless specified otherwise.

Example 1

Preparation of *Homo sapiens*- or Frog-Derived L-ldh Gene-Expressing Plasmid

A L-ldh gene having the nucleotide sequence shown in SEQ ID No. 1 was used as the *Homo sapiens*-derived L-ldh gene, and a *Xenopus laevis*-derived L-ldh gene having the nucleotide sequence shown in SEQ ID No. 2 as the frog-derived L-ldh gene. Cloning of the *Homo sapiens*- or frog-derived L-ldh gene was performed by the PCR method. A *Homo sapiens* breast cancer cell line-derived cDNA was used as the template, in PCR for preparation of the *Homo sapiens*-derived L-ldh gene. In preparation of the cDNA from the *Homo sapiens* breast cancer cell line, it was prepared by culturing and collecting the *Homo sapiens* breast cancer cell line (MCF-7), extracting the total RNA with a TRIZOL Reagent (manufactured by manufactured by Invitrogen), and performing reverse transcription reaction using the obtained total RNA as the template and a Super Script Choice System (Invitrogen). Specifically, these operations were performed according to the protocols respectively attached. In PCR for preparation of a frog-derived L-ldh gene, a phagemid DNA prepared from a *Xenopus laevis* kidney-derived cDNA library (manufactured by STRATAGENE) was used as the template. The phagemid DNA was prepared according to the protocol attached.

The *Homo sapiens*-derived L-ldh gene-amplifying primers (SEQ ID Nos. 4 and 5) are prepared in such a manner that a XhoI-recognizing sequence is added to the 5-terminal side and a NotI-recognizing sequence to the 3-terminal side; and the frog-derived L-ldh gene-amplifying primers (SEQ ID Nos. 6 and 7) are prepared in such a manner that a SalI-recognizing sequence is added to the 5-terminal side and a NotI-recognizing sequence to the 3-terminal side. The PCR amplification fragment is purified; the terminal phosphorylated by T4 polynucleotide Kinase (manufactured by Takara Bio Inc.); and then, the fragment ligated with a pUC118 plasmid (previously cleaved with restriction enzyme HincII and dephosphorylated). The ligation was performed using DNA Ligation Kit Ver.2 (manufactured by Takara Bio Inc.). *E. coli* DH5α competent cell (manufactured by Takara Bio Inc.) was transformed in the ligation solution, and the solution was inoculated and cultured on a LB plate media containing 50 μg/mL of an anti-biotic ampicillin overnight. The plasmid DNA was recovered from the resulting colonies and cleaved with restriction enzymes XhoI and NotI or SalI and NotI, and plasmids containing the inserted *Homo sapiens*- or frog-derived L-ldh gene were selected. The series of operations were all performed according to the protocol attached.

The pUC118 plasmid containing an inserted *Homo sapiens*- or frog-derived L-ldh gene was cleavaged with restriction enzymes XhoI and NotI or SalI and NotI; the DNA fragments were separated by agarose gel electrophoresis. The fragment containing the *Homo sapiens*- or frog-derived L-ldh gene were purified by a ordinary method. The L-ldh gene-containing fragment thus obtained was ligated with the XhoI/NotI cleavage site of the expression plasmid pTRS11 shown in FIG. 2. The plasmid DNA was recovered similarly and digested with restriction enzymes XhoI and NotI. Expression plasmids containing an inserted *Homo sapiens*- or frog-derived L-ldh gene were selected. Hereinafter, the expression plasmid thus prepared containing the *Homo sapiens*-derived L-ldh gene will be referred to as pTRS48, and the expression plasmid incorporating the frog-derived L-ldh gene, as pTRS102.

Comparative Example 1

Preparation of Bovine-Derived L-ldh Gene-Expressing Plasmid

As a comparative sample, yeast having an introduced bovine-derived L-ldh gene was prepared.

Cloning of the bovine-derived L-ldh gene (SEQ ID No. 3) was performed by the PCR method. In PCR, a phagemid DNA prepared from a bovine skeletal muscle-derived cDNA library (manufactured by STRATAGENE) according to the protocol attached was used as a template, similarly to Example 1. The gene-amplifying primers (SEQ ID Nos. 8 and 9) were prepared in such a manner that a XhoI-recognizing sequence was added to the 5-terminal side and a NotI-recognizing sequence to the 3-terminal side.

An expression plasmid having an inserted bovine-derived L-ldh gene was prepared in a similar manner to the expression plasmid having an incorporated *Homo sapiens*-derived L-ldh gene of Example 1. The expression plasmid containing an inserted bovine-derived L-ldh gene thus prepared will be referred to as pTRS49.

Example 2

Preparation of pdc1 Gene-Deficient Strain

*Saccharomyces cerevisiae* NBRC10505 in which the PDC1 gene on the genomic DNA is substituted with the TRP1 gene (hereinafter, abbreviated as Δpdc1 strain) was prepared by homologous recombination method. The Δpdc1 strain was prepared in the following manner: A DNA fragment having an inserted sequence shown in SEQ ID No. 12 at 5'-sided upstream of the TRP1 gene and an inserted sequence shown in SEQ ID No. 13 at 3'-sided downstream thereof was amplified, in PCR using plasmid pRS424 as a template and DNAs shown in SEQ ID Nos. 10 and 11 as a primer set. Amplified DNA fragments were purified, and NBRC10505 strain was transformed with 1 μg of the DNA into a tryptophan non-requiring strain. The transformant obtained was designated as SW029 strain.

Example 3

Introduction of *Homo sapiens*- or Frog-Derived L-ldh Gene-Expressing Plasmid into Yeast The SW029 strain was transformed into a uracil-non-requiring strain with pTRS48 or pTRS102 obtained in Example 1. The *Homo sapiens*- or frog-derived L-ldh gene-expressing plasmid was introduced into the transformant thus obtained, and the introduction was confirmed, by extracting the genome from the transformant and by PCR analysis using it as a template. The confirmation primers used were the primers used in cloning of each L-ldh gene (*Homo sapiens*-derived L-ldh gene: SEQ ID Nos. 4 and 5, frog-derived L-ldh gene: SEQ ID Nos. 6 and 7). As a result, the transformant with pTRS48 or pTRS102 was found to have a *Homo sapiens*- or frog-derived L-ldh gene introduced. Hereinafter, the transformants having the inserted pTRS48 and pTRS102 were designated respectively as SW029/pTRS48 strain and SW029/pTRS102 strain.

Comparative Example 2

Introduction of Bovine-Derived L-ldh Gene-Expressing Plasmid into Yeast

The SW029 was transformed into a uracil-non-requiring strain using pTRS49 obtained in Comparative Example 1. Introduction of the bovine-derived L-ldh gene-expressing plasmid was confirmed by a method similar to that in Example 3, and the oligonucleotides shown in SEQ ID Nos. 8 and 9 were used as the primers. Hereinafter, the transformant containing the pTRS49 introduced will be refereed to as SW029/pTRS49 strain.

Example 4

Introduction of a *Homo sapiens*- or Frog-Derived L-ldh Gene into Yeast Chromosome A DNA fragment of approximately 1.3 Kb including the *Homo sapiens*- or frog-derived L-ldh gene and the GAPDH terminator sequence was amplified in PCR using the pTRS48 or pTRS102 obtained in Example 1 as the amplification template and the oligonucleotides (*Homo sapiens*-derived L-ldh gene: SEQ ID Nos. 14 and 16, frog-derived L-ldh gene: SEQ ID Nos. 15 and 16) as the primer set (corresponding to Step 1 in FIG. 1). The oligonucleotides of SEQ ID Nos. 14 and 15 were designed so that a sequence of 60 bp upstream of the PDC1 gene shown in SEQ ID No. 17 was inserted.

Then, a DNA fragment at approximately 1.2 Kb including the yeast selection marker TRP1 gene was amplified in PCR using the plasmid pRS424 as an amplification template and oligonucleotides (SEQ ID Nos. 18 and 19) as a primer set, (corresponding to Step 2 in FIG. 1). The oligonucleotide SEQ ID No. 19 was so designed that a sequence of 60 bp downstream of the PDC1 gene shown in SEQ ID No. 20 is added.

Each DNA fragment was purified. The fragment obtained of 1.3 Kb including the L-ldh gene and the fragment of 1.2 Kb including the TRP 1 gene were mixed. A DNA fragment of approximately 2.5 Kb including the *Homo sapiens*- or frog-derived L-ldh gene, the GAPDH terminator and the TRP1 gene that were connected to each other was amplified in PCR using the mixture as amplification templates and the oligonucleotides (*Homo sapiens*-derived L-ldh gene: SEQ ID Nos. 14 and 19, frog-derived L-ldh gene: SEQ ID Nos. 15 and 19) as the primer set (corresponding to Step 3 in FIG. 1).

NBRC10505 strain was transformed with the DNA fragment of approximately 2.5 Kb purified; the transformant was cultured in a tryptophan deficient medium; and the transformant containing the *Homo sapiens*- or frog-derived L-ldh gene introduced downstream of the PDC1 gene promoter on the chromosome was selected.

The fact that the transformant thus obtained was a yeast containing a *Homo sapiens*- or frog-derived L-ldh gene introduced downstream of the PDC1 gene promoter on the chromosome was confirmed in the following manner: First, it was confirmed that, after the genome in the transformant was extracted, an amplification DNA fragment of approximately 2.8 Kb was obtained, in PCR using the extract as the amplification template and oligonucleotides (*Homo sapiens*-derived L-ldh gene: SEQ ID Nos. 14 and 21, frog-derived L-ldh gene: SEQ ID Nos. 15 and 21) as the primer set. The non-transformant gives an amplification DNA fragment of approximately 2.1 Kb by the same PCR. Hereinafter, the transformant having the *Homo sapiens*-derived L-ldh gene introduced downstream of the PDC1 gene promoter on the chromosome will be referred to as L5 strain, while that containing the frog-derived L-ldh gene introduced downstream of the PDC1 gene promoter on the chromosome, as B2 strain.

Example 5 and Comparative Example 3

L-Lactic Acid Fermentation Test 1

L-Lactic acid productivity tests were performed using the SW029/pTRS48 strain, SW029/pTRS102 strain and SW029/pTRS49 strain obtained as in Example 3 and Comparative Example 2.

10 mL of the medium in the composition shown in Table 1 (hereinafter, abbreviated as lactic acid fermentation medium) excluding uracil was placed in a test tube; a small amount of SW029/pTRS48 strain, SW029/pTRS102 strain or SW029/pTRS49 strain was respectively inoculated thereto and cultured at 30° C. overnight (pre-preculture). Subsequently, 100 mL of the fresh lactic acid fermentation medium excluding uracil was placed in a 500-ml Erlenmeyer flask, the entire amount of each pre-preculture solution was inoculated, and the medium was shake-cultured at 30° C. for 24 hours (preculture). Subsequently, the entire amount of each of the preculture solution after preculture for 24 was inoculated into 1 L of the lactic acid fermentation medium excluding uracil placed in a mini-jar fermentor (manufactured by Marubishi, capacity: 5 L), and the mixture was cultured under a condition of an agitation velocity of 120 rpm), a Ventilation rate of 0.1 L/min, a temperature of 30° C., and a pH of 5 (culture). The culture solution after culture for 40 hours was centrifuged; the supernatant obtained was filtered through a membrane; and the amount of L-lactic acid was determined by HPLC under the following condition:

Column: Shim-Pack SPR—H (manufactured by Shimadzu Corporation)
Mobile phase: 5 mM p-toluenesulfonic acid (flow rate: 0.8 mL/min)
Reaction solution: 5 mM p-toluenesulfonic acid, 20 mM Bistris, 0.1 mM EDTA 2Na (flow rate: 0.8 mL/min)
Detection method: Electrical conductivity
Temperature: 45° C.

Glucose Test Wako C (Wako Pure Chemical Industries) was used for measurement of glucose concentration.

Yields of L-lactic acid to sugar, as calculated from the measurement results, are summarized in Table 2.

TABLE 1

| | |
|---|---|
| Glucose | 100 g |
| Yeast Nitrogen base w/o amino acid (Difco) | 6.7 g |
| Standard 19 amino acids excluding leucine | 152 mg |
| Leucine | 760 mg |
| Inositol | 152 mg |
| p-Aminobenzoic acid | 16 mg |
| Adenine | 40 mg |
| Uracil | 152 mg |
| | Unit (l/Liter) |

TABLE 2

| | Yeast strain | Yield to sugar (%) |
|---|---|---|
| Example 5 | SW029/pTRS48 | 34 |
| Example 5 | SW029/pTRS102 | 40 |
| Comparative Example 3 | 29-1B/pTRS49 | 33 |

The results in Table 2 showed that it was possible to produce L-lactic acid by culturing the yeast having an introduced *Homo sapiens*- or frog-derived L-ldh gene at a yield to sugar higher than that by culturing the yeast having an introduced bovine-derived L-ldh gene.

Example 6

L-Lactic Acid Fermentation Test 2

A L-lactic acid productivity test was performed in a similar manner to Example 5, by using the L5 and B2 strains obtained, similarly to Example 4. The medium used was the lactic acid fermentation medium shown in Table 1.

10 mL of the lactic acid fermentation medium was placed in a test tube, and a small amount of the B2 or L5 strain was inoculated thereto, and the mixture was cultured at 30° C. overnight (pre-preculture). Subsequently, 100 mL of the fresh lactic acid fermentation medium excluding uracil was placed in a 500-ml Erlenmeyer flask; the entire amount of each prepreculture solution was inoculated; and the medium was cultured by shaking at 30° C. for 24 hours (preculture). Subsequently, the entire amount of each of the preculture solution after preculture for 24 was inoculated into 1 L of the lactic acid fermentation medium excluding uracil placed in a mini-jar fermentor (manufactured by Marubishi, capacity: 5 L), and the mixture was cultured under a condition of an agitation velocity of 120 rpm, a ventilation rate of 0.1 L/min, a temperature of 30° C., and a pH of pH 5 (culture). The culture solution after culture for 40 hours was centrifuged; the supernatant obtained was filtered through a membrane; and the amount of L-lactic acid was determined by HPLC under the condition similar to that in Example 5. Yields of L-lactic acid to sugar, as calculated from the measurement results, are summarized in Table 3.

TABLE 3

| | Yeast strain | Yield to sugar (%) |
|---|---|---|
| Example 6 | L5 | 34 |
| Example 6 | B2 | 48 |

The results in Tables 2 and 3 showed that it was possible to produce L-lactic acid by culturing the yeast having an introduced *Homo sapiens*- or frog-derived L-ldh gene at a yield to sugar not lower than that by culturing the yeast having an introduced bovine-derived L-ldh gene.

Example 7, Comparative Example 4

Activity of L-Lactate Dehydrogenase

The *Homo sapiens*- or frog-derived L-lactate dehydrogenase activity and the bovine-derived L-lactate dehydrogenase activity at pH 5 to 7 were compared by using the SW029/pTRS48 strain, SW029/pTRS102 strain and SW029/pTRS49 strain obtained in Example 3 and Comparative Example 2.

(a) Extraction of Protein from Microorganism 10 mL of SC-Ura medium was placed in a test tube; a small amount of SW029/pTRS48 strain, SW029/pTRS102 strain or SW029/pTRS49 strain was inoculated; and the mixture was cultured at 30° C. overnight (preculture). Then, 20 mL of the SC-Ura medium was placed in a 100-mL Sakaguchi flask; the preculture solution was inoculated to a concentration of 2%; and the mixture was shake-cultured for 24 hours (culture). 10 mL of the culture solution was centrifuged; the cell collected was washed with 10 mL of phosphate buffer and suspended in 1 mL of the phosphate buffer. The microorganism suspension was placed in an Eppendorf tube; an equal amount of glass beads (manufactured by SIGMA, diameter: 0.6 mm) was added; and the microorganism was homogenized in a Micro Tube Mixer (manufactured by TOMY) at 4° C. After homogenization of the microorganism as described above, the mixture was centrifuged, and the supernatant obtained was used as a L-lactate dehydrogenase solution (hereinafter, abbreviated as L-Ldh enzyme solution).

(b) Measurement of L-Lactate Dehydrogenase Activity

The concentration of the L-Ldh enzyme solution obtained in (a) was determined by using BCA Protein Assay Kit (manufactured by PIERCE), with reference to a calibration curve prepared by using bovine IgG (1.38 mg/mL, manufactured by BIO-RAD) as a standard, and the L-Ldh enzyme solution was diluted with sterile water to a concentration of 0.5 mg/mL. Then, the liquid mixtures (excluding L-Ldh enzyme solution and NADH) at 6 levels as shown in Table 4 were pipetted respectively into semimicrocuvettes, a L-Ldh enzyme solution and NADH were added and mixed immediately before initiation of measurement. The 2×BR buffer is a buffered solution of 0.08 M acetic acid, phosphoric acid, and a boric acid solution that is adjusted with 5 N NaOH to pH 5, 6, or 7.

TABLE 4

|  | Sodium pyruvate concentration 0.5 mM | Sodium pyruvate concentration 1 mM |
|---|---|---|
| L-LDH enzyme solution (0.5 mg/mL) | 100 μL | 100 μL |
| 2×BR buffer (pH 5.6, 7) | 250 μL | 250 μL |
| 15 mM NADH | 25 μL (Final concentration 0.375 mM) | 25 μL (Final concentration 0.375 mM) |
| 200 mM sodium pyruvate | 2.5 μL | 5 μL |
| Purified water | 622.5 μL | 620 μL |
| Total | 1000 μL | 1000 μL |

Decrease in absorbance at 340 nm at each level was measured by a spectrophotometer (Ultrospec3300Pro, manufactured by Amersham), and the specific activity was calculated from the Δ340 value obtained, according to the Formula (1). Measurement was performed at three levels at pH 5, 6, and 7. In the measurement above, if the specific activity of L-lactate dehydrogenase for comparison is higher than the specific activity of bovine-derived L-lactate dehydrogenase in two or higher levels among the three pH levels, the comparative L-lactate dehydrogenase is regarded as having an activity higher than that of the bovine-derived L-lactate dehydrogenase at pH 5 to 7. Calculation results are summarized in Table 5.

TABLE 5

|  | Yeast strain | pH | Sodium pyruvate concentration 0.5 mM | Sodium pyruvate concentration 1 mM |
|---|---|---|---|---|
| Example 7 | SW029/pTRS48 | 5 | 1.77 | 2.21 |
| Example 7 | SW029/pTRS48 | 6 | 6.55 | 6.49 |
| Example 7 | SW029/pTRS48 | 7 | 5.80 | 5.71 |
| Example 7 | SW029/pTRS102 | 5 | 5.67 | 6.56 |
| Example 7 | SW029/pTRS102 | 6 | 8.20 | 7.73 |
| Example 7 | SW029/pTRS102 | 7 | 7.72 | 8.74 |
| Comparative Example 4 | SW029/pTRS49 | 5 | 1.75 | 2.16 |
| Comparative Example 4 | SW029/pTRS49 | 6 | 6.52 | 6.46 |
| Comparative Example 4 | SW029/pTRS49 | 7 | 5.64 | 6.6 |

The results showed that the *Homo sapiens*- or frog-derived L-lactate dehydrogenase activity was higher than the activity of the bovine-derived L-lactate dehydrogenase at pH 5 to 7. In addition, the results in Table 2 indicated that it was possible to produce L-lactic acid by culturing the yeast having the *Homo sapiens*- or frog-derived L-ldh gene at a yield to sugar higher than that by culturing the yeast having an introduced bovine-derived L-ldh gene.

The results in Tables 2 and 5 indicated that it was possible to produce L-lactic acid by culturing the yeast containing an introduced gene coding a L-lactate dehydrogenase having a L-lactate dehydrogenase activity at pH 5 to 7 at a yield to sugar higher than that by culturing the yeast containing an introduced bovine-derived L-ldh gene.

Example 8

Preparation of Variant Gene Library by Transposon Sequence Insertion

A variant strain lacking the PDC1 gene on the genomic DNA of NBRC10505 strain (hereinafter, abbreviated as pdc1Δ0 strain) was prepared by homologous recombination. The pdc1Δ0 strain was prepared in the following manner: A DNA fragment consisting of the DNA sequence shown in SEQ ID No. 26 including 5'-upstream sided approximately 500 base pairs of the PDC1 gene was amplified in PCR using the genomic DNA of NBRC10505 strain as the template and DNA sequences shown in SEQ ID Nos. 24 and 25 as the primer set. In addition, a DNA fragment of the DNA sequence shown in SEQ ID No. 29 including 3'-downstream-sided 500 base pairs of the PDC1 gene was amplified in PCR by using the DNA sequences shown in SEQ ID Nos. 27 and 28 as the primer set. The amplified DNA fragments were purified; the two kinds of DNA fragments were mixed in the same amount; a DNA fragment of the DNA sequence shown in SEQ ID No. 30 to which 5'-upstream-sided 500 base pairs and 3'-downstream-sided 500 base pairs of the PDC1 gene are connected was amplified in PCR using the liquid mixture as a template and the DNA sequence shown in SEQ ID Nos. 24 and 28 as the primer set. The amplified DNA fragment was purified; the DNA was digested with a restriction enzyme Kpnl; and the DNA fragment obtained was connected to the plasmid pRS416 (hereinafter, abbreviated as pdc1-pRS416). The pdc1-pRS416 plasmid DNA was digested with a restriction enzyme EcoRV, and NBRC10505 strain was transformed into a uracil-non-requiring strain with using 100 ng of the DNA fragment. The transformant obtained was coated on a 1 g/L 5-fluoroorotic acid-added medium; PCR was performed using the genomic DNA of the transformant grown as a template and the DNA sequences shown in SEQ ID Nos. 31 and 32 as the primer set; and the PDC1 gene-deficient strain was selected.

Then, the pdc1Δ0 strain was transformed into a tryptophan non-requiring strain with 10 ng of the pTRS57 plasmid DNA. pTRS57 is a multicopy expression plasmid containing a structure of the bovine-derived L-ldh gene connected to the region under the control of the ADH1 promoter that is introduced into pRS424, and FIG. 3 shows the structure.

Then, the strain transformed with pTRS57 was transformed as the host with the DNA fragments obtained, by treating a transposon library prepared from the Yeast mTn Plasmid Collection (manufactured by Open Biosystems) with a restriction enzyme NotI, into a uracil-non-requiring strain.

Example 9

Screening of High L-Lactic Acid-Production Efficiency Yeast Strain by Using Lactic Acid Productivity as an Indicator The recombinant strain prepared in Example 8 was cultured in a SC-Ura medium at a temperature of 30° C. overnight. 10 μl of the culture solution was inoculated into 1 ml of the SC-Ura medium, and the mixture was shake-cultured at a temperature of 30° C. After culture for 40 hours, the culture solution was centrifuged, and the lactic acid concentration of the supernatant was determined. F-kit (L-lactic acid) (manufactured by J.K. International) was used for quantitative determination of lactic acid.

As a result, as shown in Table 6, the strain prepared by introducing pTRS57 into the parent pdc1Δ0 strain generated 3.6 g/l of lactic acid in 40 hours. Thus, a strain having the PDR13 gene with an inserted transposon (hereinafter, abbreviated as pdr13::mTn strain) was selected, as a strain producing lactic acid in reaction period of 40 hours in an amount greater than the pdc1Δ0/pTRS57 strain.

TABLE 6

| Recombinant strain | Lactic acid concentration after 40 hours (g/l) |
|---|---|
| pdr13::mTn | 8.5 |
| pdc1Δ0 | 3.6 |

Example 10

Preparation of PDR13 Gene-Inserted Variant and Evaluation of L-Lactic Acid Productivity DNA sequence analysis showed that the transposon sequence was inserted between the nucleotides 1599th and 1560th from the start codon of the PDR13 gene on the genomic DNA in the pdr13::mTn strain obtained in Example 9. For reconstruction of insertion mutation in the PDR13 gene, a DNA fragment having an added sequence shown in SEQ ID No. 35 in 5'-upstream and an added sequence shown in SEQ ID No. 36 in the 3' downstream of the TRP1 gene was amplified. In PCR using the plasmid pRS424 as the template and the DNAs consisting of the DNA sequences shown in SEQ ID Nos. 33 and 34 as the primer set. The PCR amplification fragment was purified, and the pdc1Δ0 strain was transformed into a tryptophan non-requiring strain with 10 μg of the DNA. The transformant obtained was designated as pdr13__1599 strain. Then, the pdr13__1599 strain was transformed into a uracil-non-requiring strain with the pTRS48 obtained in Example 1. The transformant obtained was designated as pdr13__1599/pTRS48 strain.

The recombinant strain prepared, pdr13__1599/pTRS48 strain, was shake-cultured in 10 ml of a SC-Ura medium at a temperature of 30° C. overnight. 100 μl of the culture solution was inoculated into 10 mL of the SC-Ura medium, and the mixture was shake-cultured at a temperature of 30° C. The culture solution was collected in an amount of 1 ml after culture for 16 hours, 24 hours and 40 hours; each of the culture solutions was centrifuged; and the lactic acid concentration in the supernatant was determined. F-kit (L-lactic acid) (manufactured by J.K. International) was used for quantitative determination of lactic acid. Results are summarized in Table 7.

TABLE 7

| Recombinant strain | Lactic acid concentration after 16 hours (g/L) | Lactic acid concentration after 24 hours (g/L) | Lactic acid concentration after 40 hours (g/L) |
|---|---|---|---|
| pdr13__1599 | 2.82 | 4.74 | 7.18 |
| pdc1Δ0 | 2.18 | 3.97 | 5.77 |

Example 11

Preparation of PDR13 Gene Region-Deficient Strain and Evaluation of L-Lactic Acid Productivity A variant pdr13__100 strain lacking the region of the PDR13 gene from 1560th to 1716th bases was prepared and the lactic acid productivity was determined. The pdc1Δ0/pTRS48 strain and the pdr13__1599/pTRS48 strain were shake-cultured in 10 ml of a SC-Ura liquid medium at a temperature of 30° C. overnight. 100 μl of the culture solution was inoculated into 10 ml of the new SC-Ura liquid medium; 1 ml of the sample was collected respectively after culture for 16 hours, 24 hours and 40 hours; and the amount of lactic acid produced was determined quantitatively by the HPLC method described in Example 5.

As a result, as shown in Table 8, the strain produced lactic acid in an amount greater than the parent pdc1Δ0/pTRS48 strain.

TABLE 8

| Recombinant strain | Lactic acid concentration after 16 hours (g/L) | Lactic acid concentration after 24 hours (g/L) | Lactic acid concentration after 40 hours (g/L) |
|---|---|---|---|
| pdr13__100 | 3.25 | 4.81 | 6.60 |
| pdc1Δ0 | 2.18 | 3.97 | 5.77 |

The above region-deficient strain was prepared in the following manner: A DNA fragment having an added sequence shown in SEQ ID No. 35 in the 5'-upstream and an added sequence shown in SEQ ID No. 38 in the 3'-downstream of the TRP1 gene was amplified in PCR using the plasmid pRS424 as the template and the DNAs consisting of the DNA sequences shown in SEQ ID Nos. 33 and 37 as the primer set. The PCR amplification fragment was purified, and the pdc1Δ0 strain was transformed into a tryptophan non-requiring strain with 1 μg of the DNA. The transformant obtained was designated as pdr13__100 strain. Then, the pdr13__100 strain was transformed into a uracil-non-requiring strain with the pTRS48. The transformant obtained was designated as pdr13__100/pTRS48 strain.

Example 12

Preparation of PDR13 Gene Region-Deficient Strain and Evaluation of L-Lactic Acid Productivity A DNA fragment having the sequence shown in SEQ ID No. 35 in the 5'-upstream and the sequence shown in SEQ ID No. 38 in the 3'-downstream of the HIS3 gene was amplified in PCR using the plasmid pRS423 as the template and the DNAs consisting of the DNA sequences shown in SEQ ID Nos. 33 and 37 as the primer set. The PCR amplification fragment was purified, and the SW029 strain obtained in Example 2 was transformed into a histidine-non-requiring strain with 1 pg of the DNA. The transformant obtained was designated as Δpdr13__100 strain. Then, the Δpdr13__100 strain was transformed into a uracil-non-requiring strain with the pTRS48. The transformant obtained was designated as pdr13__100/pTRS48 strain.

The recombinant strain prepared, pdr13__100/pTRS48, was shake-cultured in 10 ml of a SC-Ura medium at a temperature of 30° C. for 24 hours. 10 ml of the culture solution was inoculated into 100 ml of the SC-Ura medium, and the mixture was shake-cultured at a temperature of 30° C. for 24 hours. 100 ml of the culture solution was inoculated into 2.0 L of the SC-Ura medium, and the mixture was cultured at a temperature of 30° C. in a mini-jar fermentor, and the amount of the L-lactic acid produced was determined quantitatively. The culture was performed under the following condition:

Fermenter: Bioneer-N (manufactured by Marubishi)
Cultivation temperature: 30° C.
Aeration rate: 0.5 vvm
Agitation velocity: 800 rpm
pH: 5.0
Neutralizing agent: 2N NaOH solution As a result, as shown in Tables 9 and 10, the strain produced L-lactic acid in a greater amount than the parent Δpdc1/pTRS48 strain.

TABLE 9

| Recombinant strain | Lactic acid amount after 40 hours (g) |
|---|---|
| Δpdr13_100 | 32.9 |
| Δpdc1 | 26.0 |

TABLE 10

| Recombinant strain | Lactic acid amount after 120 hours (g) |
|---|---|
| Δpdr13_100 | 76.1 |
| Δpdc1 | 71.7 |

Example 13

Preparation of a Yeast Having a Temperature-Sensitive Variant ADH1 Gene

A NBRC10505 strain yeast in which the ADH1 gene on the genomic DNA is substituted with the URA3 gene was prepared by homologous recombination. A DNA fragment having an added sequence shown in SEQ ID No. 45 in 5'-upstream and an added sequence shown in SEQ ID No. 46 in the 3'-downstream of the HIS3 gene was amplified by PCR using the plasmid pRS313 as the template and DNAs consisting of the DNA sequences shown in SEQ ID Nos. 43 and 44 as the primer set. The amplified DNA fragment was purified, and a NBRC10505 strain was transformed into a uracil-non-requiring strain with 1 μg of the DNA. The transformant obtained was designated as Δadh1 strain.

Then, using the genomic DNA of the NBRC10505 strain as the template and the primers shown in SEQ ID Nos. 47 and 48, a DNA fragment including upstream 700 bp region of the ADH1 gene, the ADH1 structural gene, and the downstream 200 bp region was amplified. The gene-amplifying primers (SEQ ID Nos. 47 and 48) were so prepared that a SacI-recognizing sequence is added to the 5-terminal side and a SmaI-recognizing sequence to the 3-terminal side. The amplified fragment was ligated with the HincII/BAP-processed fragment of pUC118. The desirable plasmid pUC118_ADH1 was obtained by a ordinary method.

Then, pUC118_ADH1 was digested with restriction enzymes SacI and SmaI, and the reaction solution was subjected to agarose electrophoresis. A fragment of approximately 2 Kb was separated, and the DNA fragment was extracted from the gel separated. The DNA fragment extracted was inserted into pRS316 by ligation reaction, to give a desired plasmid pRS316_ADH1.

Then, for introduction of mutation on the ADH1 gene on the plasmid by gap reparation method, pRS316_ADH1 was digested with restriction enzymes BalI and PflFI, to give a ring-opened plasmid lacking the ADH1 structural gene. Fragments of approximately 7 Kb were separated from the restriction enzyme reaction solution by agarose electrophoresis, and the desired DNA fragment was extracted from the gel obtained. In addition, the DNA fragment was precipitated with ethanol according to a ordinary method.

Subsequently, a mutagenic ADH1 gene fragment for mutagenesis by the gap reparation method was prepared. The fragment was prepared using the primers shown in SEQ ID Nos. 49 and 50 and a random mutagenesis kit BD Diversify PCR Random Mutagenesis Kit (manufactured by CLONTECH). The operation was made according to the instruction attached. The fragment obtained was precipitated with ethanol according to a ordinary method and concentrated to 200 ng/μl.

The Δadh1 strain was transformed into a uracil-non-requiring strain with 500 ng of the ring-opened plasmid obtained and 1 micro-g of the mutagenic ADH1 gene fragment. The host Δadh1 strain, which is a strain lower in sugar-consumption efficiency, does not grow rapidly in glucose-containing media. Thus after transformation, strains forming colonies on the SC-Ura medium within two days were chosen as strains in which the variant ADH1 gene on the introduced pRS316_ADH1 DNA had an alcohol dehydrogenase activity at the cultivation temperature.

The pRS316_ADH1-containing transformant chosen was spread on the SC-Ura medium at a concentration of about 100 colonies per plate, and cultured thereon at 25° C. for 48 hours, the colonies are replicated onto four new SC-Ura plate media, and the plates were cultured at 25° C., 30° C., 34° C., and 37° C. for comparison of the growth state. Colonies that do not grow at a cultivation temperature of 30° C., 34° C., or 37° C. were regarded as the strains in which the ADH1 on the plasmid became temperature sensitive, and obtained. Among them, yeast strains that became temperature-sensitive at 34° C., pADH1ts-1, pADH1ts-2, and pADH1ts-3, were obtained.

Plasmids were extracted respectively from the three temperature-sensitive pADH1ts strains obtained. E. coli DH5α was transformed with each extracted plasmid, and the plasmid was obtained from the culture solution according to an ordinary method. The plasmids obtained were digested with restriction enzymes SacI and SmaI, and the ΔADH1 strain was transformed with the cleavage solution. The culture solution obtained was spread on a YPAD plate medium and cultured at 25° C. for 48 hours. Because the Δadh1 strain does not grow on a glucose-containing plate, the grown colonies were considered that the Δadh1 gene locus is recombined with a temperature-sensitive ADH1 gene, and regarded as a yeast having the temperature-sensitive ADH1 gene integrated into the chromosome (ADH1ts-1, ADH1ts-2, or ADH1ts-3).

The DNA sequences of the temperature-sensitive ADH1ts gene loci contained in the temperature-sensitive yeasts obtained, ADH1ts-1, ADH1ts-2, and ADH1ts-3, were determined, and the amino acid sequences thereof were determined from the sequences, showing that they had respectively the primary amino acid sequences shown in SEQ ID Nos. 40, 41 and 42.

Example 14

Measurement of the Alcohol Dehydrogenase Activity of Yeasts Having a Temperature-Sensitive Variant ADH1 Gene The alcohol dehydrogenase activity of the yeasts having the temperature-sensitive variant ADH1 gene obtained in Example 13, ADH1ts-1, ADH1ts-2, and ADH1ts-3, was determined. Each strain was inoculated in 20 mL of a YPD liquid medium and cultured at 30° C. for 20 hours. The colonies were collected, and 200 µl of 50 mM potassium phosphate buffer solution (pH 7.0) and 0.2 g of glass beads (manufactured by SIGMA, diameter: 0.6 mm) were added; and the mixture was voltexed at 4° C. for 30 minutes. After voltexing, the suspension was centrifuged, and the supernatant collected. The protein concentration of each homogenate supernatant was determined by using BCA Protein Assay Kit (manufactured by Pierce), according to a calibration curve prepared by using bovine IgG (1.38 mg/mL, manufactured by Bio-Rad) as the standard.

Then, the alcohol dehydrogenase activity of each strain was determined. The activity was determined, as 10 µl of the supernatant obtained was added to 190 µl of a reaction solution containing 53 mM potassium phosphate buffer solution (pH 7.0), 20 mM sodium pyruvate, 0.19 mM reduced nicotinamide dinucleotide (NADH), 0.21 mM thiamine pyrophosphate, and 5.3 mM magnesium chloride, and the change in absorbance at a wavelength of 340 m after addition was monitored with a spectrophotometer (Ultraspec3300Pro, manufactured by Amersham Biosciences). The change in absorbance obtained is substituted into the Δ340 nm in Formula (2) above, and the specific activity of each alcohol dehydrogenase was calculated, by dividing the alcohol dehydrogenase activity by the concentration of each protein. The results are summarized in Table 11.

Comparative Example 5

Measurement of the Alcohol Dehydrogenase Activity Wild-Type Yeast

In addition, the alcohol dehydrogenase activity of NBRC10505 was determined, similarly to Example 14. The results are summarized in Table 11.

TABLE 11

| | Strain | Specific activity of alcohol dehydrogenase (mmol/min/µg protein) |
|---|---|---|
| Example 14 | ADH1ts-1 | 0.0068 |
| Example 14 | ADH1ts-2 | 0.0294 |
| Example 14 | ADH1ts-3 | 0.007 |
| Comparative Example 5 | NBRC10505 | 0.1431 |

The results of Example 14 and Comparative Example 5 shown in Table 11 indicated that the yeasts having a temperature-sensitive variant ADH1 gene (ADH1ts-1, ADH1ts-2 or ADH1ts-3 strains) obtained in Example 13 have an alcohol dehydrogenase activity at 30° C. lower than that of the wild-type strain (NBRC10505 strain).

Example 15

Lactic Acid Fermentation by a Yeast Having a Temperature-Sensitive Variant ADH1 Gene A fermentation test in a mini-jar fermentor was performed by using the yeast obtained by introducing the L-ldh gene into the transformant prepared in Example 13, and the amounts of the lactic acid and ethanol produced by the yeast having a temperature-sensitive variant ADH1 gene were determined by measuring the L-lactic acid production.

In the present Example, a *Homo sapiens*-derived L-ldh gene having the nucleotide sequence shown in SEQ ID No. 1 was used as the L-ldh gene.

Transformants having the *Homo sapiens*-derived L-ldh gene respectively introduced downstream of the PDC1 gene promoter on the chromosome of ADH1ts-1, ADH1ts-2, and ADH1ts-3 strains were prepared in a manner similar to Example 4. Confirmation of the fact that it was a yeast having the *Homo sapiens*-derived L-ldh gene introduced downstream of the PDC1 gene promoter on the chromosome was also made, in a similar manner to Example 4. Hereinafter, the transformants having the *Homo sapiens*-derived L-ldh gene introduced down-stream of the PDC1 gene promoter on the chromosome will be referred to respectively as ADH1ts-1-L, ADH1ts-2-L, and ADH1ts-3-L strains.

10 mL of a lactic acid fermentation medium was placed in a test tube; a small amount of the ADH1ts-1-L, ADH1ts-2-L or ADH1ts-3-L strain was inoculated, and the mixture was shake-cultured at 30° C. and 120 rpm overnight, to give a pre-preculture solution. Then, 100 mL of the fresh lactic acid fermentation medium was placed in a 500-mL Erlenmeyer flask, the entire amount of each pre-preculture solution was inoculated therein, and the mixture was shake-cultured at 30° C. for 24 hours (preculture). Subsequently, the mixture was then cultured in a mini-jar fermentor containing 1 L of the lactic acid fermentation medium, and the amount of L-lactic acid produced was determined quantitatively. The culture in the mini-jar fermentor was performed under the following condition:

Fermenter: Bioneer-N (manufactured by Mauricio)
Cultivation temperature: 30° C.
Aeration rate: 0.1 vvm
Agitation velocity: 120 rpm
pH: 5.0
Neutralizing agent: 1 N NaOH solution The culture solution after culture for 40 hours was collected, and the amounts of L-lactic acid and ethanol produced were determined. The ethanol production amount was determined and evaluated by using a Shimadzu GC-2010 capillary gas chromatograph TC-1 (GL Science) 15 meter L.×0.53 mm I.D., df=1.5 µm and a hydrogen flame ionization detector. The results are summarized in Table 12.

Comparative Example 6

Lactic Acid Fermentation by Yeast Having Wild-Type ADH1 Gene

Additionally, a fermentation test in a jar fermentor was performed in a similar manner to Example 15 by using the L5 strain having the wild-type alcohol dehydrogenase prepared in Example 4, and the amounts of L-lactic acid and ethanol produced were measured. The results are summarized in Table 12.

Example 16

Lactic Acid Fermentation by Yeast Having a Temperature-Sensitive Variant ADH1 Gene at a Cultivation Temperature of 32° C.

A fermentation test in a jar fermentor of the transformant ADH1ts-1-L strain prepared in Example 15 was preformed at a temperature of 32° C., which is the cultivation temperature at which the alcohol dehydrogenase contained in the ADH1ts-1-L strain becomes temperature-sensitive, and the amount of the lactic acid and ethanol produced by the yeast having a temperature-sensitive variant ADH1 gene were determined by measuring the amount of L-lactic acid produced.

10 mL of a lactic acid fermentation medium was placed in a test tube; a small amount of the ADH1ts-1-L strain was inoculated, and the mixture was shake-cultured at 30° C. and 120 rpm overnight, to give a pre-preculture solution. Then, 100 mL of the fresh lactic acid fermentation medium was placed in a 500-mL Erlenmeyer flask; the entire amount of each preculture solution was inoculated therein; and the mixture was shake-cultured at 30° C. for 24 hours (preculture). Subsequently, the mixture was cultured in a mini-jar fermentor containing 1 L of the lactic acid fermentation medium, and the amount of L-lactic acid produced was determined quantitatively. The culture was performed under the following condition:

Fermenter: Bioneer-N (manufactured by Marubishi)
Cultivation temperature: 32° C.
Aeration rate: 0.1 vvm
Agitation velocity: 120 rpm
pH: 5.0
Neutralizing agent: 1 N NaOH solution The culture solution after culture for 40 hours was collected, and the amounts of L-lactic acid and ethanol produced were determined. These results are summarized in Table 12.

TABLE 12

|  | Strain | Cultivation temperature (° C.) | Lactic acid concentration (g/L) | Ethanol concentration (g/L) |
| --- | --- | --- | --- | --- |
| Example 15 | ADH1ts-1-L | 30 | 43.0 | 28.7 |
| Example 15 | ADH1ts-2-L | 30 | 37.3 | 30.2 |
| Example 15 | ADH1ts-3-L | 30 | 40.8 | 29.3 |
| Comparative Example 6 | L5 | 30 | 33.0 | 32.0 |
| Example 16 | ADH1ts-1-L | 32 | 53.8 | 21.9 |

As shown in Table 12, culture of the yeasts having a temperature-sensitive variant ADH1 gene (ADH1ts-1-L, ADH1ts-2-L, and ADH1ts-3-L strains) at a cultivation temperature of 30° C. (Example 15) was found to result in increase in the amount of the L-lactic acid produced and decrease in the amount of ethanol produced, compared to the culture of the yeast having the wild-type alcohol dehydrogenase (L5 strain) at the same temperature (Comparative Example 6).

In addition, culture of the yeast having a temperature-sensitive variant ADH1 gene (ADH1ts-1-L strain) at a cultivation temperature of 32° C. (Example 16) was found to result in further increase in the amount of L-lactic acid produced and further decrease in the amount of ethanol produced, compared to the fermentation test results at a cultivation temperature of 30° C. (Example 15).

Example 17

Preparation of Δpdc1 and Δpdc5 Double Deficient Strain

A yeast lacking the PDC5 gene on the genomic DNA of the NBRC10506 strain was prepared in the following manner: A URA3 gene DNA fragment of 1.3 Kb was amplified in PCR using the plasmid pRS406 as the amplification template and the oligonucleotides (SEQ ID Nos. 54 and 55) as the primer set. The amplified DNA fragment was purified, and the NBRC10506 strain was transformed into a uracil-non-requiring strain with the DNA fragment. The transformant cell obtained should be a Δpdc5 deficient strain in which the PDC5 gene on the genomic DNA was substituted with the URA3 gene. For confirmation, amplification products obtained in PCR using the genomic DNA as the amplification template and the oligonucleotides shown in SEQ ID Nos. 56 and 57 as the primer set were analyzed by agarose electrophoresis. When the PDC5 gene on the genomic DNA is substituted with the URA3 gene, an amplification product of 1.2 Kb is obtained. On the other hand when it is not substituted, an amplification product of 1.9 Kb is obtained. Because the 1.2-Kb product was isolated, the transformant was considered to be the SW011 strain lacking the PDC5 gene. The Δpdc1Δpdc5 double deficient strain was prepared in the following manner: The SW011 strain obtained above and the SW029 strain obtained in Example 2 were mated, to give a diploid cell. Asci of the diploid cell were formed in a sporulation medium. The ascus was dissected with a micromanipulator, and each spore was grown in YPAG medium, to give each haploid cell. The auxotrophy of the haploid cell obtained was analyzed. The desired Δpdc1Δpdc5 double deficient strain likely requires neither of uracil or tryptophan. After determining the auxotrophy, the strain required neither of uracil or tryptophan. Deletion of the PDC1 and PDC5 genes was confirmed in PCR using the genomic DNA of the uracil/tryptophan non-requiring strain obtained as the amplification template and the oligonucleotides shown in SEQ ID Nos. 58 and 59, and the oligonucleotides shown in SEQ ID Nos. 56 and 57 as primer sets. The Δpdc1Δpdc5 double deficient strain was designated as SW012 strain. The SW012 strain was found not to grow on glucose as a single carbon source.

In addition, a HIS3 gene DNA fragment of 1.3 Kb was amplified, in PCR using the plasmid pRS403 as the amplification template and the oligonucleotides shown in SEQ ID Nos. 54 and 55 as the primer set. The amplified DNA fragment was purified, and the NBRC10506 strain was transformed into a histidine-non-requiring strain with the DNA fragment. The transformant obtained should be a Δpdc5 deficient strain in which the PDC5 gene on the genomic DNA is substituted with the HIS3 gene. For confirmation, amplification products obtained in PCR using the genomic DNA as the amplification template and the oligonucleotides shown in SEQ ID Nos. 56 and 57 as the primer set were analyzed by agarose electrophoresis. When the PDC5 gene on the genomic DNA is substituted with the HIS3 gene, an amplification product of 1.3 Kb is obtained. On the other hand when it is not substituted, an amplification product of 1.9 Kb is obtained. Because the 1.3-Kb product was isolated, the transformant was considered to be the SW013 strain lacking the pdc5 gene. The Δpdc1Δpdc5 double deficient strain was prepared in the following manner: The SW013 strain obtained above and the SW029 strain obtained in Example 2 were mated, to give a diploid cell. Asci of the diploid cell was formed in an ascus-forming medium. The ascus was dissected with a micromanipulator, and each spore was grown in YPAG medium, to give each haploid cell. The auxotrophy of the haploid cell obtained was analyzed. The desired Δpdc1Δpdc5 double deficient strain likely requires neither of histidine or tryptophan. After study on auxotrophy, deletion of the PDC1 and PDC5 genes was confirmed in PCR using the genomic DNA of the histidine/tryptophan non-requiring strain obtained as the amplification template and the oligonucleotides shown in SEQ ID Nos. 58 and 59 and the oligonucleotides shown in SEQ ID Nos. 56 and 57 as primer sets. The Δpdc1Δpdc5 double deficient strain was designated as SW014 strain. The SW014 strain was found not to grow on glucose as a single carbon source.

Example 18

Preparation of pdc5 Temperature-Sensitive Variant Gene

An amplification DNA fragment of 2.7 Kb containing the PDC5 gene was obtained, in PCR using the genomic DNA of the BY4741 strain as the template and the oligonucleotides shown in SEQ ID Nos. 60 and 61 as the primer set. The fragment was digested with NotI and then, inserted into the NotI cleavage site of the plasmid pRS316 previously digested with NotI. The SW013 strain was transformed into a uracil-non-requiring strain with the plasmid pRS316-PDC5 obtained. It was confirmed that the transformant had a recovered growth on glucose as a single carbon source and a favorable growth rate at 37° C. The plasmid pRS316-PDC5 was recovered from the transformant by an ordinary method, and the DNA sequence of 2.7 Kb inserted into pRS316 was identified by a ordinary method, showing that the pRS316-PDC5 contained the PDC5 gene.

Subsequently, an amplification DNA fragment of 1.7 Kb coding the PDC5 was obtained, in PCR using the plasmid pRS316-PDC5 as the amplification template and the oligonucleotide shown in SEQ ID Nos. 62 and 63 as the primer set and by using a BD Diversify PCR Random Mutagenesis Kit (manufactured by Clontech). PCR using the kit raises mutagenetic probability during DNA amplification, and thus, the fragment of 1.7. Kb obtained is more likely to contain a variant fragment, compared to the fragment obtained by normal PCR. The SW014 strain was transformed into a uracil-non-requiring strain, with the fragment of 1.7 Kb obtained and a plasmid fragment obtained by digestion of the plasmid pRS316-PDC5 with restriction enzymes Van91I and Bpu1102I and subsequent linearization, and a transformant growing in a SC-Ura medium as warmed at 25° C. was selected. The fragment of 1.7 Kb and the linearized plasmid were connected to each other by homologous recombination by a gap reparation method, and only the cells containing the cyclized plasmid grew. The transformants obtained was replicated on a fresh SC-Ura medium, and warmed at 34° C. Among the replicate transformants, two transformants not growing at 34° C. were selected, and designated as pdc5 temperature-sensitive variants, pdc5ts-9 and pdc5ts-11. The plasmids were recovered from the transformants by an ordinary method, and the sequences of the 1.7-Kb amplification DNA fragment was specified. As a result, the pdc5ts-9 was a single-nucleotide substitution mutation from C to T at the 1697th nucleotide in the structural gene DNA shown in SEQ ID No. 52, and the pdc5ts-11 was a single-nucleotide substitution mutation from C to T at the 701th nucleotide in the structural gene DNA shown in SEQ ID No. 53. The plasmids were designated as pRS316-pdc5ts9 and pRS316-pdc5ts11 respectively having a pdc5 temperature-sensitive mutation allele.

Example 19

Preparation of pdc5ts Variant

Plasmid pRS316-pdc5ts9 and pRS316-pdc5ts11 were digested with NotI, to give a 2.7-Kb fragment containing pdc5ts9 and pdc5ts11 variant genes. The SW012 strain was trans-formed into a uracil-requirement strain with the fragment, and the transformants growing in the 5-FOA medium as warmed at 25° C. were selected. The transformants obtained were replicated on a fresh SC medium and warmed at 34° C. Among the replicated transformants, transformants not growing at 34° C. were selected, and designated as pdc5ts9 temperature-sensitive variant SW015 strain and pdc5ts11 temperature-sensitive variant SW016 strain.

Example 20

Properties of pdc5ts Variant

The PDC activity of the PDC wild-type strain, Δpdc1 deficient strain and Δpdc1 pdc5 temperature-sensitive strain was determined.

(a) Extraction of Protein from Microorganism

Small amounts respectively of NBRC10505 strain, SW029 strain, SW015 strain, and SW016 strain were collected from an agar medium and inoculated in 3 mL of a YPD liquid medium and cultured overnight (preculture). The preculture solution was inoculated into 20 mL of the new YPD liquid medium to a concentration of 1%, and shake-cultured in a 100-mL Sakaguchi flask at a temperature of 30° C. for 24 hours (culture). 10 mL of the culture solution was centrifuged to collect the cell, which was washed with 10 mL of a phosphate buffer and suspended in 1 mL of the phosphate buffer. The microorganism suspension was transferred into an Eppendorf tube, the equal amount of glass beads (manufactured by SIGMA, diameter: 0.6 mm) were added, and the microorganism was homogenized in a Micro Tube Mixer (manufactured by TOMY) at 4° C. The microorganism thus homogenized was centrifuged, and the supernatant obtained was used as a PDC enzyme solution.

(b) Measurement of PDC Activity

The concentration of the PDC enzyme solution obtained in (a) was determined by using BCA Protein Assay Kit (manufactured by Pierce) according to a calibration curve prepared by using bovine IgG (1.38 mg/mL, manufactured by Bio-Rad) as the standard, and each PDC enzyme solution was diluted with sterile water to a concentration of 2 mg/mL. Then, a liquid mixture excluding the PDC enzyme solution and NADH was pipetted into a semimicrocuvette at the amount shown in Table 13, a PDC enzyme solution and NADH were added and mixed immediately before measurement.

TABLE 13

| Sample | 100 μL (2 mg/mL) |
|---|---|
| Buffer (20 mM bis-Tris, 50 mM KCl, pH 6) | 425 μL |
| 50 mM MgCl$_2$ | 200 μL (final 5 mM) |
| 2 mM Thiaminepyrophosphate | 200 μL (final 0.2 mM) |
| 10 mM NADH | 30 μL (final 0.3 mM) |
| 22 U/μL ADH | 20 μL |
| 200 mM Pyruvate Na | 25 μL (final 5 mM) |

Decrease in absorbance at 340 nm of each PDC enzyme solution was determined by a spectrophotometer (Ultrospec3300Pro, manufactured by Amersham), and the specific activity of each PDC at 5 mM of sodium pyruvate was calculated by applying the Δ value obtained into the Formula (1). The results are summarized in Table 14.

TABLE 14

| Yeast strain | NBRC10505 | SW029 | SW015 | SW016 |
|---|---|---|---|---|
| PDC1 gene | Wild-type | Absent | Absent | Absent |
| PDC5 gene | Wild-type | Wild-type | Variant | Variant |
| Specific activity of PDC enzyme (mU) | 3290 | 1630 | 1040 | 670 |

The results showed that the specific PDC activity of the pdc5ts9 temperature-sensitive variant SW015 strain and the pdc5ts11 temperature-sensitive variant SW016 strain having the variant PDC5 gene was ⅓ or less of that of NBRC10505 strain and lower than that of SW029 strain, and thus, it was possible to obtain a yeast having a lower specific PDC activity by obtaining a PDC5 gene temperature-sensitive variant yeast.

Example 21

Lactic Acid Fermentation Test pdc5 with Temperature-Sensitive Variant (No. 1))

A lactic acid fermentation test was carried out by using the pdc5 temperature-sensitive variant thus obtained. The *Homo sapiens*-derived L-ldh gene was introduced into the pdc5 temperature-sensitive variant, by transforming the SW015 and SW016 strains into uracil-non-requiring strains with the *Homo sapiens*-derived L-ldh gene-expressing plasmid pTRS48 obtained in Example 1. The lactic acid fermentation medium shown in Table 1 was used in the lactic acid fermentation test.

The concentration of the product lactic acid was evaluated by the HPLC method described in Example 5.

The optical purity of L-lactic acid was determined by a HPLC method under the following condition:
Column: TSK-gel Enantio L1 (manufactured by Toso Corporation)
Mobile phase: 1 mM aqueous copper sulfate solution
Flow rate: 1.0 ml/min
Detection method: UV 254 nm
Temperature: 30° C.

The optical purity of L-lactic acid is calculated according to the following Formula:

Optical purity (%)=100×(L−D)/(L+D)

Here, L represents the concentration of L-lactic acid, and D represents the concentration of D-lactic acid.

Glucose Test Wako C (Wako Pure Chemical Industries) was used for measurement of the glucose concentration.

The condition for the lactic acid fermentation test is shown below:
Fermenter: Bioneer-N (manufactured by Marubishi)
Medium: 1 L lactic acid fermentation medium
Cultivation temperature: 30° C.
Aeration rate: 100 ml/min
Agitation velocity: 200 l/min
pH: 5.0
Neutralizing agent: 1 N NaOH solution.

First, the SW015 and SW016 strains transformed with pTRS48 were shake-cultured respectively in 5 ml of lactic acid fermentation medium in a test tube (pre-preculture). The preculture solution was inoculated into 100 ml of fresh lactic acid fermentation medium, and the mixture was shake-cultured in a 500-ml Sakaguchi flask for 24 hours (preculture). The preculture solution was transferred into the fermenter for the lactic acid fermentation test. The results are summarized in Table 15.

Example 22

Lactic Acid Fermentation Test with pdc5 Temperature-Sensitive Variant (No. 2))

A lactic acid fermentation test of the pdc5 temperature-sensitive variant above was carried out. The frog-derived L-ldh gene was introduced by transforming the SW015 and SW016 strains with the frog-derived L-ldh gene-expressing plasmid pTRS102 obtained in Example 1. The lactic acid fermentation medium shown in Table 1 sterilized under high-pressure steam (121° C., 15 minute) was used in the lactic acid fermentation test.

The concentration of the product lactic acid was evaluated by the HPLC method described in Example 5.

The optical purity of L-lactic acid was determined by the HPLC method described in Example 21.

First, the SW015 and SW016 strains transformed with pTRS102 were shake-cultured respectively with 5 ml of lactic acid fermentation medium in a test tube overnight (pre-preculture). The pre-preculture solution was inoculated in 100 ml of fresh lactic acid fermentation medium, and the mixture was shake-cultured in a 500-ml Sakaguchi flask for 24 hours (preculture). The preculture solution was transferred into the fermenter for the lactic acid fermentation test. The results are summarized in Table 15.

Comparative Example 7

Lactic Acid Fermentation by Using pdc5 Wild-Type Strain (No. 1))

A fermentation test of the PDC5 wild-type strain was also carried out in a Comparative Example. The fermentation test was carried out by using SW029/pTRS48 obtained in Example 3 under the same condition as that when the pdc5 temperature-sensitive variant was used. The results are summarized in Table 15.

Comparative Example 8

Lactic Acid Fermentation of pdc5 Wild-Type Strain (No. 2))

Further, a fermentation test was carried out of SW029/pTRS102 obtained in Example 3 under the same condition as that when the pdc5 temperature-sensitive variant was used. The results are summarized in Table 15.

TABLE 15

| | Yeast strain | ldh gene | PDC5 gene | Fermentation period (hour) | Lactic acid yield to sugar (%) |
|---|---|---|---|---|---|
| Example 21 | SW015 | *Homo sapiens*-derived | Variant | 65 | 39 |
| Example 21 | SW016 | *Homo sapiens*-derived | Variant | 66 | 41 |
| Comparative Example 7 | SW029 | *Homo sapiens*-derived | Wild-type | 60 | 30 |
| Example 22 | SW015 | *Xenopus laevis*-derived | Variant | 65 | 48 |
| Example 22 | SW016 | *Xenopus laevis*-derived | Variant | 66 | 48 |
| Comparative Example 8 | SW029 | *Xenopus laevis*-derived | Wild-type | 60 | 41 |

The results showed that the lactic acid yield to sugar is improved when lactic acid fermentation is performed of a pdc5ts9 temperature-sensitive variant SW015 strain or a pdc5ts11 temperature-sensitive variant SW016 strain having an introduced *Homo sapiens*- or frog-derived L-ldh gene, compared to when it is performed of the PDC5 gene-deficient SW029 strain. The fact shows that it is possible to produce lactic acid efficiently by using yeast lower in specific activity containing the variant PDC5 gene.

INDUSTRIAL APPLICABILITY

The yeast and lactic acid produced by the yeast have a variety of applications including fermentation products such as sake, miso, soy sauce, pickles, and dairy products, acidifiers substituting citric acid and tartaric acid, cool drinks, pharmaceuticals and the like. In addition, lactic acid, which is also used favorably as the raw material for polylactic acid in the resin field, is an extremely useful substance.

It is possible to produce lactic acid having such a variety of applications efficiently and more cost-effectively by using the yeast and the production method by using the yeast.

What is claimed is:

1. A yeast cell able to produce L-lactic acid comprising a gene comprising a nucleotide sequence selected from the group consisting of the nucleotide sequence of SEQ ID. No. 2 or a nucleotide sequence having at least 95% sequence homology to the nucleotide sequence of SEQ ID NO:2 wherein the nucleotide sequence is functionally linked to a promoter and encodes a L-lactate dehydrogenase obtained or isolated from *Xenopus laevis*.

2. The yeast according to claim 1, wherein the gene encoding a L-lactate dehydrogenase is introduced at a position downstream of a promoter enabling expression of the gene encoding a L-lactate dehydrogenase.

3. The yeast according to claim 1, wherein the gene encoding a L-lactate dehydrogenase is integrated on a chromosome at a position downstream of the promoter for pyruvate decarboxylase 1 gene.

4. The yeast according to claim 1, further comprising an introduced gene functionally linked to a promoter and encoding a mutant alcohol dehydrogenase selected from the group consisting of the amino acid sequences of SEQ ID Nos. 40, 41 and 42, wherein the variant alcohol dehydrogenase exhibits temperature sensitivity, wherein the alcohol dehydrogenase activity disappears or reduces at 30° C. in cultivation temperature relative to a wild-type strain.

5. The yeast according to claim 1, wherein the yeast belongs to Genus *Saccharomyces*.

6. The yeast according to claim 1, wherein the yeast is *Saccharomyces cerevisiae*.

7. A method of producing L-lactic acid, comprising culturing the yeast according to claim 1.

8. A method of producing L-lactic acid, comprising culturing the yeast according to claim 1 at 25 to 37° C.

9. A method of producing L-lactic acid, comprising culturing the yeast according to claim 1 at 30 to 34° C.

* * * * *